(12) United States Patent
Kubota et al.

(10) Patent No.: US 8,962,336 B2
(45) Date of Patent: Feb. 24, 2015

(54) SOIL DIAGNOSIS AND IMPROVEMENT METHOD

(75) Inventors: Kenzo Kubota, Kusatsu (JP); Hiroyuki Ishimori, Kusatsu (JP); Yoshiki Matsumiya, Kusatsu (JP); Ryoichi Fukagawa, Kusatsu (JP); Motoki Kubo, Kusatsu (JP); Nobuyuki Kadokura, Kusatsu (JP); Akio Kanemori, Kusatsu (JP)

(73) Assignee: The Ritsumeikan Trust, Kyoto (JP)

( * ) Notice: Subject to any disclaimer, the term of this patent is extended or adjusted under 35 U.S.C. 154(b) by 659 days.

(21) Appl. No.: 13/256,757

(22) PCT Filed: Mar. 19, 2010

(86) PCT No.: PCT/JP2010/054892
§ 371 (c)(1),
(2), (4) Date: Sep. 15, 2011

(87) PCT Pub. No.: WO2010/107121
PCT Pub. Date: Sep. 23, 2010

(65) Prior Publication Data
US 2012/0014748 A1  Jan. 19, 2012

(30) Foreign Application Priority Data
Mar. 19, 2009 (JP) ................................. 2009-068788

(51) Int. Cl.
*G01N 33/24* (2006.01)
*A01C 21/00* (2006.01)

(52) U.S. Cl.
CPC .............. *A01C 21/007* (2013.01); *G01N 33/24* (2013.01)
USPC .................................... 436/25; 702/2; 702/19

(58) Field of Classification Search
USPC .......................................... 436/25; 702/2, 19
See application file for complete search history.

(56) References Cited

U.S. PATENT DOCUMENTS

| | | | | |
|---|---|---|---|---|
| 5,668,719 | A | * | 9/1997 | Bobrov et al. ..................... 702/2 |
| 5,768,128 | A | * | 6/1998 | Thompson et al. ............... 702/2 |
| 6,055,480 | A | | 4/2000 | Nevo et al. |
| 6,599,747 | B1 | * | 7/2003 | Reid et al. ....................... 436/25 |
| 8,340,910 | B1 | * | 12/2012 | Magro et al. ..................... 702/2 |
| 2002/0103601 | A1 | * | 8/2002 | Hayes et al. ..................... 702/2 |
| 2013/0046468 | A1 | * | 2/2013 | Baker et al. ...................... 702/2 |
| 2013/0151153 | A1 | * | 6/2013 | Hatano ............................ 702/2 |

FOREIGN PATENT DOCUMENTS

JP  2001-523008  11/2001
WO  99/24930  5/1999

OTHER PUBLICATIONS

Hipps, N. A. et al, Journal of the Science of Food and Agriculture 1991, 55, 377-387.*
Picard, C. et al, Applied and Environmental Microbiology 1992, 58, 2717-2722.*
Zhou, J. et al, Applied and Environmental Microbiology 1996, 62, 316-322.*
Luizao, F. J. et al, Forest Ecology and Management 1998, 102, 291-303.*
Michelsen, A. et al, New Phytologist 1999, 143, 523-538.*
Miller, D. N. et al, Applied and Environmental Microbiology 1999, 65, 4715-4724.*
McDonald, M. A. et al. Forest Ecology and Management 2000, 139, 257-278.*
Arunachalam, A. et al. Forest Ecology and Management 2002, 159, 231-239.*
Jonasson, S. et al, Soil Biology & Biochemistry 2004, 36, 1129-1139.*
Lupwayi, N. Z. et al, Canadian Journal of Soil Science 2004, 84, 403-410.*
Niinemets, U. et al, Acta Oecologica 2005, 28, 345-356.*
Hungria, M. et al, Canadian Journal of Plant Science 2006, 86, 927-939.*
Lupwayi, N. Z. et al, Canadian Journal of Soil Science 2006, 86, 767-778.*
He, J.-Z. et al, Environmental Microbiology 2007, 9, 2364-2374.*
Rowe, E. C. et al, Environmental Pollution 2008, 155, 201-207.*
International Search Report issued Jun. 22, 2010 in International (PCT) Application No. PCT/JP2010/054892 of which the present application is the national stage.
Takanobu Sato et al., Abstracts of Japan Society for Bioscience, Biotechnology, and Agrochemistry meeting 2008, p. 202, 3A10a07, Mar. 5, 2008, with English translation.
Yasuhiro Moroe et al., Abstracts of the 60th Annual Meeting of the Society for Biotechnology, Japan, p. 81, 2Ba10, Jul. 11, 2008, with English translation.

* cited by examiner

*Primary Examiner* — Arlen Soderquist
(74) *Attorney, Agent, or Firm* — Wenderoth, Lind & Ponack, L.L.P.

(57) ABSTRACT

Disclosed are a soil diagnosis method for diagnosing soil using a cycle activity indicator which is calculated using the following factors (I) to (III): (I) the ammonia reduction rate in target soil; (II) the activity of forming phosphoric acid from phytic acid in the target soil; and (III) the activity of forming potassium from compost in the target soil, and (IV) the soil bacteria count in the soil; and a soil quality control method; and a soil improvement method.

8 Claims, 8 Drawing Sheets

EVALUATION VALUE 40.0
EXAMPLE OF SOIL EVALUATION BASED ON NITROGEN CYCLE ACTIVITY
(SOIL No. 2)

ANALYSIS OF EFFECT OF AUTOTROPHIC AMMONIUM OXIDIZING BACTERIA ON NITROGEN CYCLE ACTIVITY IN SOIL
A: SOIL No. 1, B: No. 2, ◇: INOCULATION OF NO STRAIN,
○: STRAIN A, △: STRAIN B.

EVALUATION OF PHOSPHORUS CYCLE ACTIVITY

EVALUATION OF POTASSIUM CYCLE ACTIVITY

SOIL DIAGNOSIS AND IMPROVEMENT METHOD

TECHNICAL FIELD

The present invention mainly relates to a novel soil diagnosis method in which soil bacteria count and cycle activity of substances are used as indicators, and a soil quality control method and a soil improvement method which utilize the diagnosis method.

BACKGROUND ART

In various environments, for example, in soil, microorganisms play an important role in converting and cycling substances. For example, in order for nitrogenous fertilizer to be converted in agricultural land so as to be taken in by agricultural crops, microorganisms need to perform "nitrification".

Owing to the progress of the chemosynthesis technology, farming methods using chemical fertilizer have been widely performed in the postwar period. However, due to an increased demand for consumers' safety and safe agricultural products, or for the sake of sustainable agricultural production, shift to organic farming or natural farming is increasingly taking place in various regions. In these farming methods, practical use of ecosystems in soil is important. In addition, agricultural products use and absorb components in soil to grow, and thus appropriate evaluation, control, and improvement of soil are considered to contribute to improvement in profitability and productivity.

However, hitherto known soil evaluation has mainly involved analysis for chemical farming, and thus the evaluation has mainly been based on physicochemical properties such as concentration of inorganic ions and pH, whereas activity of microorganisms has not been taken into consideration (see non-patent literatures 1 and 2).

Thus, it has been impossible to clearly determine whether soil is suitable for cultivation of agricultural crops using organic farming or natural farming, or whether soil requires improvement.

CITATION LIST

Non-Patent Literature

[NPL 1] "Soil Standard Analysis/Measurement Method", editorial supervision by Japanese Society of Soil Science and Plant Nutrition, edited by Soil Standard Analysis/Measuring Method Committee, Hakuyu-Sha, 107-117, 1986

[NPL 2] "Tsuchi no Kankyo-ken", editorial supervision by Shingo Iwata et. al., Fuji Techno System, 223 to 228, 1997

SUMMARY OF INVENTION

Technical Problem

A main objective of the present invention is to provide a soil diagnosis method, a soil quality control method, and a soil improvement method which take into consideration cycles of substances caused by soil microorganisms, and in particular to provide methods for diagnosing, controlling and improving the quality of agricultural land suitable for vegetation.

Solution to Problem

In view of the above problem, the inventors of the present application have earnestly studied techniques of evaluating and diagnosing soil in which soil microorganism activity is reflected. Consequently, through combination of soil bacteria count and analyses relating to nitrogen, phosphorus, and potassium, the inventors found that an appropriate soil diagnosis can be realized, and has finally completed the present invention through further study.

Specifically, the present invention relates to a soil diagnosis method, a soil quality control method, and a soil improvement method as described below.

Item 1: a soil diagnosis method for diagnosing soil using a cycle activity indicator which is calculated using the following (I) to (III):
(I) an ammonia reduction rate in target soil;
(II) an activity of forming phosphoric acid from phytic acid in the target soil; and
(III) an activity of forming potassium from compost in the target soil, and
(IV) a soil bacteria count in soil.

Item 2: the diagnosis method according to item 1, wherein the cycle activity indicator indicates a proportion, with respect to the area of an equilateral triangle having, as vertices, a preset reference value of an ammonia reduction rate, a preset reference value of an activity of forming phosphoric acid from phytic acid, and a preset reference value of an activity of forming potassium from compost,
of the area of a triangle having, as vertices, points of measured values of (I) the ammonia reduction rate, (II) the activity of forming phosphoric acid from phytic acid, and (III) the activity of forming potassium from compost, the points being located on line segments extending from the center of gravity of the equilateral triangle to the corresponding vertices of the equilateral triangle.

Item 3: a soil diagnosis method for diagnosing soil using at least
A) a nitrogen cycle activity indicator calculated using the following (A-1) to (A-3):
   (A-1) a soil bacteria count in target soil;
   (A-2) an ammonia reduction rate in the target soil; and
   (A-3) a nitrous acid reduction rate in the target soil,
B) a phosphorus cycle activity indicator calculated using the following (B-1) to (B-3):
   (B-1) the soil bacteria count in the target soil;
   (B-2) an activity of forming phosphoric acid from phytic acid in the target soil; and
   (B-3) an activity of forming phosphoric acid from compost in the target soil, and
C) a potassium cycle activity indicator calculated using the following (C-1) to (C-3):
   (C-1) the soil bacteria count in the target soil;
   (C-2) a potassium release rate in the target soil; and
   (C-3) an activity of forming potassium from compost in the target soil.

Item 4: the diagnosis method according to item 3, wherein the nitrogen cycle activity indicator indicates a proportion, with respect to the area of an equilateral triangle having, as vertices, a preset reference value of a soil bacteria count, a preset reference value of an ammonia reduction rate, and a preset reference value of a nitrous acid reduction rate,
of the area of a triangle having, as vertices, points of measured values of (A-1) the soil bacteria count, (A-2) the ammonia reduction rate, and (A-3) the nitrous acid reduction rate, the points being located on line segments extending from the center of gravity of the equilateral triangle to the corresponding vertices of the equilateral triangle.

Item 5: the diagnosis method according to item 3 or 4, wherein the phosphorus cycle activity indicator indicates a proportion,
with respect to the area of an equilateral triangle having, as vertices, the preset reference value of the soil bacteria count, a preset reference value of an activity of forming phosphoric acid from phytic acid, and a preset reference value of an activity of forming phosphoric acid from compost, of the area of a triangle having, as vertices, points of measured values of (B-1) the soil bacteria count, (B-2) the activity of forming phosphoric acid from phytic acid, and (B-3) the activity of forming phosphoric acid from compost, the points being located on line segments extending from the center of gravity of the equilateral triangle to the corresponding vertices of the equilateral triangle.

Item 6: the diagnosis method according to any of items 3 to 5, wherein the potassium cycle activity indicator indicates a proportion,
with respect to the area of an equilateral triangle having, as vertices, the preset reference value of the soil bacteria count, a preset reference value of a potassium release rate, and a preset reference value of an activity of forming potassium from compost,
of the area of a triangle having, as vertices, points of measured values of (C-1) the soil bacteria count, (C-2) the potassium release rate, and (C-3) the activity of forming potassium from compost, the points being located on line segments extending from the center of the gravity of the equilateral triangle to the corresponding vertices of the equilateral triangle.

Item 7: a soil quality control method for controlling the quality of soil, the method comprising: temporally performing the diagnosis method according to any of items 1 to 6; and analyzing temporal changes of the indicators.

Item 8: a soil improvement method comprising: performing the diagnosis method according to any of items 1 to 6; and performing treatment for improving the indicators in accordance with a result of the diagnosis.

Hereinafter, the present invention will be described in further detail.

1. Soil Diagnosis Method
1.1. Soil Diagnosis Method (1)

A soil diagnosis method (1) of the present invention is characterized by diagnosing soil using a cycle activity indicator calculated using the following (I) to (III):
(I) the ammonia reduction rate in target soil;
(II) the activity of forming phosphoric acid from phytic acid in the target soil; and
(III) the activity of forming potassium from compost in the target soil, and
(IV) soil bacteria count in soil.

(I) Ammonia Reduction Rate

In the present invention, the ammonia reduction rate in target soil represents a value indicating the reduction rate of the concentration of an ammonia compound administered into the target soil.

Specifically, the ammonia reduction rate can be calculated as a value obtained from the following formula, when an ammonia compound is administered into the target soil.

Ammonia reduction rate (%)=$[1-(N^1-N^2)/N^1] \times 100$ (In the formula, $N^1$ represents the amount of ammonia nitrogen on an ammonia compound administration day, and $N^2$ represents the amount of ammonia nitrogen after a predetermined period of time following the ammonia compound administration).

The ammonia compound administration day means a day on which an ammonia compound is administered into the target soil. The amount of ammonia nitrogen on the ammonia compound administration day can be represented as the amount of ammonia nitrogen on Day 0 of administration.

In addition, the predetermined period of time after the ammonia compound administration means a day after a predetermined period of time elapsed from administration of the ammonia compound into the target soil. For example, the amount of ammonia nitrogen after three days has elapsed from the administration of the ammonia compound into the target soil can be represented as the amount of ammonia nitrogen on Day 3 of administration.

The length of the predetermined period of time can be set as appropriate, and is preferably three to seven days, more preferably three days after administration. If the period of time is shorter or extremely longer than this, it is difficult to recognize difference in the activity.

In other words, as the ammonia reduction rate in the target soil, a value obtained from the following formula:

$$\text{Ammonia reduction rate}(\%) = \left(1 - \frac{\text{amount of ammonia nitrogen on Day } 0 - \text{amount of ammonia nitrogen on Day } 3}{\text{amount of ammonia nitrogen on Day } 0}\right) \times 100 \quad \text{[Formula 1]}$$

can be preferably used.

The amount of ammonia nitrogen means the amount of ammonia nitrogen ($NH_4^+$) per unit dry weight of target soil.

The amount of ammonia nitrogen can be measured using an indophenol method, a leaching method using potassium chloride, high-performance liquid chromatography, and the like. More specifically, the amount of ammonia nitrogen can be measured using a method of determination of the amount of ammonia nitrogen employed in the examples herein.

The type of the ammonia compound to be administered into the target soil is not particularly limited, and examples of the ammonia compound include ammonium salts such as ammonium sulfate, ammonium chloride, ammonium nitrate, and ammonium carbonate. Among these, ammonium sulfate which is common agricultural fertilizer is used preferably.

In addition, the amount of the ammonia compound to be administered into the target soil is not particularly limited. In consideration of the concentration of nitrogen-containing compounds in common field soil, the amount of the ammonia compound is about 30 to 100 μg-N/g-dry soil, preferably about 60 to 70 μg-N/g-dry soil per unit dry weight of target soil.

The ammonia reduction rate reflects conversion efficiency from ammonia nitrogen to nitrite nitrogen. It is considered that if the reduction rate is higher, many ammonium oxidizing bacteria are contained in the target soil, or ammonium oxidizing bacteria whose activity per unit biomass is high are contained in the target soil. It is also considered that if the reduction rate is lower, there are a smaller number of ammonium oxidizing bacteria.

(II) Activity of Forming Phosphoric Acid from Phytic Acid

In the present invention, the activity of forming phosphoric acid from phytic acid in target soil represents a value indicating the activity of conversion of phytic acid administered into the target soil.

Specifically, the activity of forming phosphoric acid from phytic acid in the target soil can be calculated as a value obtained from the following formula, when phytic acid is administered into the target soil.

Activity of forming phosphoric acid from phytic acid (%)= $[(P^3-P^2)/P^1] \times 100$ (In the formula, $P^1$ represents the amount of phosphoric acid in phytic acid, $P^2$ represents the amount of water-soluble phosphoric acid on a phytic acid administration day, and $P^3$ represents the amount of water-soluble phosphoric acid after a predetermined period of time following the phytic acid administration.)

The amount of phosphoric acid in phytic acid can be calculated from the amount of phytic acid administered based on the fact that 1 mol of phytic acid contains 6 molecules of phosphoric acid.

The phytic acid administration day means a day on which phytic acid is administered into the target soil. The amount of water-soluble phosphoric acid on the phytic acid administration day can be represented as the amount of water-soluble phosphoric acid on Day 0 of administration.

In addition, the predetermined period of time after the phytic acid administration means a day after a predetermined period of time elapsed from administration of phytic acid into the target soil. For example, the amount of water-soluble phosphoric acid after three days has elapsed from the administration of phytic acid into the target soil can be represented as the amount of water-soluble phosphoric acid on Day 3 of administration.

The length of the predetermined period of time can be set as appropriate, and is preferably three to seven days, more preferably three days after administration. If the period of time is shorter or extremely longer than this, it is difficult to recognize difference in the activity.

In other words, as the activity of forming phosphoric acid from phytic acid in the target soil, a value obtained from the following formula:

[Formula 2]

$$\text{Activity of forming phosphoric acid from phytic acid}(\%) = \left( \frac{\text{amount of water soluble phosphoric acid on Day 3} - \text{amount of water soluble phosphoric acid on Day 0}}{\text{amount of phosphoric acid in phytic acid}} \right) \times 100$$

can be preferably used.

The amount of water-soluble phosphoric acid means the amount of water-soluble phosphoric acid per unit dry weight of target soil.

The amount of water-soluble phosphoric acid can be measured using a molybdenum blue method, high-performance liquid chromatography, and the like. More specifically, the amount of water-soluble phosphoric acid can be measured using a method of determination of the amount of water-soluble phosphoric acid employed in the examples herein.

The amount of phytic acid to be administered into the target soil is not particularly limited, but is about 0.5 to 5% (w/w), preferably about 1 to 2% (w/w) per unit dry weight of target soil.

The activity of forming phosphoric acid from phytic acid reflects conversion efficiency from phytic acid to water-soluble phosphoric acid. It is considered that if the activity is higher, phosphorus contained in plant bodies is more likely to be used. Thus, it is considered that if the activity is higher, the soil has excellent quality, and consequently, the amount of phosphorus fertilizer to be introduced externally can be minimized.

On the other hand, it is considered that if the activity is lower, phosphorus in plant bodies is less likely to be used. Thus, it is considered that if the activity is lower, the soil has insufficient quality, and consequently, compost, phosphorus fertilizer, or the like needs to be introduced externally.

(III) Activity of Forming Potassium from Compost

In the present invention, the activity of forming potassium from compost in target soil represents a value indicating the activity of conversion of potassium in compost administered into the target soil into free potassium.

The compost is the same as that described above in relation to the phosphorus cycle indicator, and examples of compost include: vegetable compost such as bark compost; livestock compost such as poultry manure compost, cow manure compost, and swine manure compost; and seaweed compost. These types of compost may be used individually, or two or more types of compost may be used in combination.

Among these types of compost, the bark compost contains a large amount of potassium, and thus enables more appropriate evaluations. Normally, the content of total potassium ($K_2O$) in bark compost is 0.1% or more (dry matter).

In addition, the manner in which compost is administered is not limited. Compost mixed with culture soil may be used. In this case, the mixing rate of the compost with respect to the total culture soil is 10 to 50% in weight, and preferably about 25 to 35%.

The activity of forming potassium from compost in compost soil can be calculated as a value obtained from the following formula, when compost is administered into the target soil.

Activity of forming potassium from compost (%)=$[(K^6-K^5)/K^4] \times 100$ (In the formula, $K^4$ represents the amount of potassium in compost, $K^5$ represents the amount of potassium release on a compost administration day, and $K^6$ represents the amount of potassium release a predetermined period of time after the compost administration.)

The amount of potassium in compost can be determined in accordance with publicly known methods. For example, ammonium acetate aqueous solution is added to compost, followed by filtration, the filtrate, i.e., a potassium extraction liquid thus obtained, is measured using an atomic absorption spectrophotometer, and whereby the amount of potassium can be obtained.

The compost administration day means a day on which compost is administered into the target soil. For example, the amount of potassium release on the compost administration day can be represented as the amount of potassium release on Day 0 of administration.

In addition, the predetermined period of time after the compost administration means a day after a predetermined period of time elapsed from administration of compost into the target soil. For example, the amount of potassium release after three days has elapsed from the administration of compost into the target soil can be represented as the amount of potassium release on Day 3 of administration.

The length of the predetermined period of time can be set as appropriate, and is preferably three to seven days, more preferably three days after administration. If the period of time is shorter or extremely longer than this, it is difficult to recognize difference in the activity.

In other words, as the activity of forming potassium from compost in the target soil, a value obtained from the following formula:

$$\text{Activity of forming potassium from compost}(\%) = \left( \frac{\begin{array}{c} \text{amount of potassium release on Day 3} - \\ \text{amount of potassium release on Day 0} \end{array}}{\text{amount of potassium in compost}} \right) \times 100$$

[Formula 3]

can be preferably used.

The amount of potassium release can be measured in the same manner as that described below.

The activity of forming potassium from compost reflects conversion efficiency from potassium in the compost to free potassium. It is considered that if the activity is higher, potassium in the compost is more likely to be used. Thus, it is considered that if the activity is higher, the soil has excellent quality, and consequently the amount of potassium to be introduced externally can be minimized.

On the other hand, it is considered that if the activity is lower, potassium in the compost is less likely to be used. Thus, it is considered that if the activity is lower, the soil has insufficient quality, and consequently potassium needs to be introduced externally.

(IV) Soil Bacteria Count

In the present invention, the soil bacteria count represents the soil bacteria count obtained based on the amount of DNA present per unit weight of sample taken from target soil.

If the unit weight is 1 g, the amount can be represented as a unit of the number per unit weight of target soil (or sample) (cells/g-soil or cells/g-sample).

The amount of DNA herein indicates an amount of DNA present per unit weight of sample taken from the target soil. More particularly, the amount indicates the total amount of DNA present per unit weight of sample regardless of the origin of DNA.

The soil bacteria count can be obtained by converting the amount of DNA present per unit weight of sample taken from the target soil, using an appropriate technique.

For example, the soil bacteria count can be obtained by preliminarily obtaining correlation between the soil bacteria count in soil and the amount of DNA using a measuring means such as a microscope, and matching an amount of DNA measured from a taken sample with the correlation.

In an example of preferred embodiments, the soil bacteria count is obtained by converting the amount of DNA per unit weight of sample taken from the target soil, using the following formula.

$$Y=1.7\times10^8 X (R^2=0.96)$$

[Y; soil bacteria count (cells/g-soil), X; amount of eDNA (μg/g-soil)]

The sample taken from the target soil represents soil taken (sampled) from the above target soil. The method for sample taking is not particularly limited, but any publicly known method can be used as appropriate.

Sample taking condition may also be set as appropriate. However, in order to judge the state of microorganisms in the target soil appropriately, it is preferable that sample taking is performed while avoiding those periods in which the target soil is not in a normal state due to rain or the like.

The amount of DNA per unit weight of sample taken from the target soil can be measured by eluting DNA present in a sample taken from the target soil for diagnosis, and determining the amount of the DNA.

It is preferable to measure the amount of DNA in a sample taken from the target soil immediately after the sample is obtained. However, the obtained sample may be stored for about one day to three weeks at low temperature (e.g., at about −4 to −80 degrees, more preferably about −20 to −80 degrees).

The method for eluting DNA from all the microorganisms contained in a sample is not particularly limited, unless the method causes significant decomposition or shearing of DNA and results in adverse effects on the determination.

An exemplary embodiment of the method for eluting DNA is to treat a sample with a DNA elution solution.

An example of the DNA elution solution used herein is a solution generally used for eluting DNA from bacteria.

Specifically, as the DNA extraction solution, a solution containing a deoxyribonuclease inhibitor such as EDTA or EGTA, a cationic surfactant, an anionic surfactant, and/or a buffer solution containing these is preferably used. Alternatively, the buffer solution may contain proteolytic enzymes such as proteinase K, thermolysin, subtilisin, and the like. The blending proportion of each component may be set as appropriate in the range without significantly inhibiting elution of DNA.

In DNA elution using the above-described DNA elution solution, conditions for DNA elution are not particularly limited. For example, DNA elution can be performed by adding, to an amount of 1 g of soil to be subjected to elution treatment, the above-described DNA elution solution at an amount of 2 to 20 ml, preferably 5 to 15 ml, and more preferably 8 to 12 ml.

In addition, the elution temperature can be set as appropriate depending on the DNA elution solution to be used or the type of soil to be subjected to elution treatment.

The elution time varies depending on the type of DNA elution solution to be used, the type of soil to be subjected to elution treatment, the elution temperature, and the like, and cannot be specified uniformly. However, an example of the elution time is 0.1 to 4 hours, preferably 0.2 to 2 hours, and more preferably 0.3 to 1 hours.

The amount of DNA eluted in the manner as described above is determined, whereby the amount of DNA present in the target soil can be obtained.

The method of determination of the amount of DNA is not particularly limited. For example, eluted DNA can be purified as necessary, and collected, and then the amount is determined using a publicly known or conventional method of determination of the amount of DNA.

Specifically, an example of the method of determination of the amount of DNA is a method in which DNA collected by purification is subjected to agarose gel electrophoresis, and stained with ethidium bromide, and thereby the fluorescence intensity of bands of DNA on the gel is measured.

Alternatively, a method may be used in which DNA collected by purification is dissolved in a buffer solution, and the absorbance at 260 nm of the solution is measured.

The method of purifying DNA is not particularly limited, either, and the DNA purification can be performed in accordance with ordinary procedures. An example of the method of purifying DNA is a method comprising the steps of: centrifuging a solution having been subjected to DNA elution treatment as described above and collecting the supernatant liquid; adding, to the above-obtained supernatant liquid, an impurity removing solution, such as chloroform or chloroform-isoamyl alcohol, which undergoes layer separation from the supernatant liquid, followed by mixing; extracting from the mixed solution the layer containing DNA and removing impurities; and adding a DNA precipitant, such as isopropyl alcohol, ethanol, or polyethylene glycol, to the layer containing DNA which is obtained in the precedent step to precipitate and collect DNA.

DNA extraction efficiency varies depending on the type of the target soil. Thus, it is preferable that DNA extraction efficiency is preliminarily measured with respect to samples, and correction is made for each sample of the target soil based on the extraction efficiency thereby to obtain the amount of DNA in the sample.

The DNA extraction efficiency described herein means the proportion of the amount of DNA actually eluted from a sample taken from the target soil and determined with respect to the amount of DNA contained in the sample.

Based on the amount of DNA measured as above, and in accordance with the above-described method, the soil bacteria count can be obtained.

More specifically, the soil bacteria count can be obtained using a method described in the examples herein.

The total amount of DNA derived from all bacteria present in a sample reflects overall characteristics and state of the target soil. Thus, the soil bacteria count obtained based on the amount of DNA present per unit weight of sample taken from the target soil can be an indicator for understanding the characteristics of the soil and the state of performance of bacteria in the soil.

It is considered that if the soil bacteria count is greater, the activity of conversion of substances in the soil including, for example, various organic substances, nitrogen-containing compounds, and phosphorus-containing compounds is high. On the other hand, it is considered that if the soil bacteria count is lower, contaminants remain in the soil, growth of soil bacteria is inhibited, and consequently the activity of conversion of substances is low. If the soil bacteria count is lower than $2 \times 10^8$ cells/g-soil, the cycle activity lowers.

(V) Evaluation of Cycle Activity

Above-described (I), (II), (III), and (IV) are important factors for cycles of nitrogen, phosphoric acid, and potassium in soil, and combined analysis of these factors is a key for appropriate diagnosis.

If the soil bacteria count is equal to or greater than $2 \times 10^8$ cells/g-soil, and the following conditions are satisfied in relation to (I), (II), and (III), it is judged that the soil is suitable for vegetation, whereas if any of the following conditions is not satisfied, it is judged that the soil is not suitable for vegetation.

(I) The reference value of the ammonia reduction rate can be set as follows. That is, ammonium sulfate 60 μg-N/g-dry soil is administered into target soil, and the amount of ammonia nitrogen on Day 0 and the amount of ammonia nitrogen on Day 3 are measured. When a value obtained using the above formula is 100%, the value can be set as the reference value. If a measured value is 30% or more, preferably 60% or more, it can be evaluated that the soil has excellent activity of conversion of ammonia. Generally, the concentration of nitrogen-containing compounds in field soil is about 60 μg-N/g-dry soil, and thus if the reduction rate in such an amount is 100%, it can be evaluated that the soil has necessary and sufficient activity of conversion of ammonia.

The reference value of the activity of forming phosphoric acid from phytic acid can be set as follows. That is, phytic acid is administered into the target soil at 1% (w/w) per unit dry weight of target soil, and the amount of water-soluble phosphoric acid on Day 0 and the amount of water-soluble phosphoric acid on Day 3 are measured. When a value obtained using the above formula is 100%, the value can be set as the reference value. If a measured value is 10% or more, preferably 30% or more, it can be evaluated that the soil has excellent activity of forming phosphoric acid from phytic acid.

The reference value of the activity of forming potassium from compost can be set as follows. That is, compost is administered into the target soil at 1% (w/w) per unit dry weight of target soil, and the amount of potassium release on Day 0 and the amount of potassium release on Day 3 are measured. When a value obtained using the above formula is 100%, the value can be set as the reference value. If a measured value is 5% or more, preferably 20% or more, it can be evaluated that the soil has excellent activity of forming potassium from compost.

Although a method of calculating a cycle activity indicator through combination of the above-described factors (I), (II), and (III) is not particularly limited, it is preferable to calculate the cycle activity indicator as follows. That is, an equilateral triangle is formed with the preset reference value of the ammonia reduction rate, the preset reference value of the activity of forming phosphoric acid from phytic acid, and the preset reference value of the activity of forming potassium from compost set as the vertices, whereas a triangle is formed with points of measured values of (I) the ammonia reduction rate, (II) the activity of forming phosphoric acid from phytic acid, and (III) the activity of forming potassium from compost set as the vertices, the points being located on line segments extending from the center of gravity of the equilateral triangle to the corresponding vertices. The proportion of the area of the triangle with respect to that of the equilateral triangle is calculated as the cycle activity indicator.

In this case, if the above conditions relating to the factors (I), (II), (III) are all satisfied; the soil bacteria count is equal to or greater than $2 \times 10^8$ cells/g-soil; and the proportion of the area of the triangle formed with the measured points as the vertices with respect to, the area of the equilateral triangle formed with the reference values as the vertices is 10 or more, preferably 30 or more, then it can be judged that the soil is suitable for vegetation. On the other hand, if the conditions or ranges are not satisfied, it can be judged that the soil is not suitable for vegetation.

Accordingly, comprehensive evaluation or judgment based on the factors (I), (II), and (III) can be made easily. Further, due to diagrammatic representation, the size of the indicator can be understood at a glance. Still further, which of the variables (I) to (III) needs to be improved is easily understandable.

If the cycle activity indicator is higher, it can be evaluated that plants are more likely to absorb nitrogen components, phosphoric acid components, and potassium components, and that efficiencies in cycles of nitrogen, phosphoric acid, and potassium in soil are preferable.

1.2. Soil Diagnosis Method (2)

The soil diagnosis method of the present invention is characterized by evaluation or diagnosis of soil using at least (A) an nitrogen cycle activity indicator, (B) a phosphorus cycle activity indicator, and (C) a potassium cycle activity indicator.

(A) Nitrogen Cycle Activity Indicator

In the present invention, the nitrogen cycle activity indicator is an indicator for analyzing the relation between conversion (including nitrification) of nitrogen-containing compounds and soil bacteria.

The nitrogen cycle activity indicator of the present invention is represented as a value calculated using (A-1) the soil bacteria count in target soil,
(A-2) the ammonia reduction rate in the target soil, and
(A-3) the nitrous acid reduction rate in the target soil.

Organic nitrogen compounds added to soil are docomposed into peptide, amino acid, and the like, and then changed into ammonia nitrogen. Further, the ammonia nitrogen ($NH_4^+$) is converted into nitrite nitrogen ($NO_2^-$), and then into nitrate nitrogen ($NO_3^-$). A denitrification reaction occurs in part, resulting in conversion into nitrogen ($N_2$).

In the above-described cycle/conversion route of organic nitrogen compounds, conversion from ammonia nitrogen into nitrite nitrogen and conversion from nitrite nitrogen into nitrate nitrogen are essential parts of the route to generate, from organic nitrogen compounds, nitric acid that can be absorbed and utilized by plants. In particular, the reaction rate of conversion from ammonia nitrogen into nitrite nitrogen in the conversion route is very low, which is rate-limiting in the series of conversion reactions of nitrogen-containing compounds. Thus, in evaluation of the nitrogen cycle activity, the ammonia-nitrogen reduction rate and the nitrite-nitrogen reduction rate are considered to be important factors.

(A-1) Soil Bacteria Count

The soil bacteria count in the target soil is as per that described in above (IV) cycle activity indicator.

(A-2) Ammonia Reduction Rate

The ammonia reduction rate in the target soil is as per that described in above (I) cycle activity indicator.

(A-3) Nitrous Acid Reduction Rate

In the present invention, the nitrous acid reduction rate in the target soil represents a value indicating the reduction rate of the concentration of nitrite nitrogen ($NO_2^-$) administered into the target soil.

Specifically, the nitrous acid reduction rate can be calculated as a value obtained from the following formula, when a nitrous acid compound is administered into the target soil.

$$\text{Nitrous acid reduction rate}(\%) = [1-(N^3-N^4)/N^3] \times 100$$

(In the formula, $N^3$ represents the amount of nitrite nitrogen on a nitrous acid compound administration day, and $N^4$ represents the amount of nitrite nitrogen after a predetermined period of time following the nitrous acid compound administration.)

The nitrous acid compound administration day means a day on which a nitrous acid compound is administered into the target soil. The amount of nitrite nitrogen on the nitrous acid compound administration day can be represented as the amount of nitrite nitrogen on Day 0 of administration.

Further, the predetermined period of time after the nitrous acid compound administration means a day after a predetermined period of time elapsed from the administration of the nitrous acid compound into the target soil. For example, the amount of nitrite nitrogen after three days has elapsed from the administration of the nitrous acid compound into the target soil can be represented as the amount of nitrite nitrogen on Day 3 of administration.

The length of the predetermined period of time can be set as appropriate, and is preferably three to seven days, more preferably three days after administration. If the period of time is shorter or extremely longer than this, it is difficult to recognize difference in the activity.

In other words, as the nitrous acid reduction rate in the target soil, a value obtained from the following formula:

$$\text{Nitrous acid reduction rate}(\%) = \left(1 - \frac{\text{amount of nitrite nitrogen on Day 0} - \text{amount of nitrite nitrogen on Day 3}}{\text{amount of nitrite nitrogen on Day 0}}\right) \times 100 \quad \text{[Formula 4]}$$

can be preferably used.

The amount of nitrite nitrogen means the amount of nitrite nitrogen ($NO_2^-$) per unit dry weight of target soil.

The amount of nitrite nitrogen can be measured using a naphthyl ethylenediamine method, high-performance liquid chromatography, and the like. More specifically, the amount of nitrite nitrogen can be measured using a method of determination of the amount of nitrite nitrogen described in the examples herein.

The nitrous acid reduction rate reflects conversion efficiency from nitrite nitrogen to nitrate nitrogen. It is considered that if the reduction rate is higher, many nitrite-oxidizing bacteria are contained in the target soil, or nitrite-oxidizing bacteria whose activity per unit biomass is high are contained in the target soil. It is also considered that if the reduction rate is lower, there are a smaller number of nitrite-oxidizing bacteria.

(A-4) Evaluation of Nitrogen Cycle Activity

Above-described (A-1), (A-2), and (A-3) are important factors for nitrogen cycle in soil, and combined analysis of these factors is a key for appropriate diagnosis.

If the following conditions are all satisfied in relation to (A-1), (A-2), and (A-3), it is judged that the soil has excellent nitrogen cycle activity, whereas if any of the following conditions is not satisfied, it is judged that the soil does not have excellent nitrogen cycle activity.

Regarding the reference value of the soil bacteria count, $3.25 \times 10^9$ cells/g-soil which is the average value of the soil bacteria count in agricultural land soil is used as 100% of the reference value. When a measured value is 10% or more, preferably 40% or more, it can be evaluated that the soil has a sufficient soil bacteria count.

The reference value of the ammonia reduction rate can be set as follows. That is, ammonium sulfate 60 μg-N/g-dry soil is administered into the target soil, and the amount of ammonia nitrogen on Day 0, and the amount of ammonia nitrogen on Day 3 are measured. When a value obtained using the above formula is 100%, the value can be set as the reference value. If a measured value is 30% or more, preferably 60% or more, it can be evaluated that the soil has excellent ammonia reduction rate. Generally, the concentration of nitrogen-containing compounds in field soil is about 60 μg-N/g-dry soil, and thus if the reduction rate in such an amount is 100%, it can be evaluated that the soil has necessary and sufficient activity of conversion of ammonia.

The reference value of the nitrous acid reduction rate can be set as follows. That is, potassium nitrite 60 μg-N/g-dry soil is administered into the target soil, and the amount of nitrite nitrogen on Day 0 and the amount of nitrite nitrogen on Day 3 are measured. When a value obtained using the above formula is 100%, the value can be set as the reference value. If a measured value is 60% or more, preferably 90% or more, it can be evaluated that the soil has excellent nitrous acid reduction rate. Generally, the concentration of nitrogen-containing compounds in field soil is about 60 μg-N/g-dry soil, and thus if the reduction rate in such an amount is 100%, it can be evaluated that the soil has necessary and sufficient activity of conversion of nitrous acid.

Although a method of calculating the nitrogen cycle activity indicator through combination of the above-described factors (A-1), (A-2), and (A-3) is not particularly limited, it is preferable to calculate the nitrogen cycle activity indicator as follows. That is, an equilateral triangle is formed with the preset reference value of the soil bacteria count, the preset reference value of the ammonia reduction rate, and the preset reference value of the nitrous acid reduction rate set as the vertices, whereas a triangle is formed with points of measured values of (A-1) the soil bacteria count, (A-2) the ammonia reduction rate, and (A-3) the nitrous acid reduction rate set as the vertices, the points being located on line segments extending from the center of gravity of the equilateral triangle to the corresponding vertices. The proportion of the area of the triangle with respect to that of the equilateral triangle is calculated as the nitrogen cycle activity indicator.

Accordingly, comprehensive evaluation or judgment based on the factors (A-1), (A-2), and (A-3) can be made easily. Further, as illustrated in FIG. 2, due to diagrammatic representation, the size of the indicator can be understood at a glance. Still further, which of the variables (A-1) to (A-3) needs to be improved is easily understandable.

In this case, if the above conditions relating to the factors (A-1), (A-2), (A-3) are satisfied; and the proportion of the area of the triangle formed with the measured points as the vertices with respect to the area of the equilateral triangle formed with the reference values as the vertices is 10 or more, preferably 40 or more, then it can be judged that the soil has excellent nitrogen cycle activity. On the other hand, if the above values are not satisfied, it can be judged that the soil does not have excellent nitrogen cycle activity.

The nitrogen cycle activity indicator can be calculated using a calculation method described in the examples herein, more specifically.

If the nitrogen cycle activity indicator is higher, it can be evaluated that plants are more likely to absorb nitrogen components, and that the efficiency in nitrogen cycle in the soil is preferable.

(B) Phosphorus Cycle Activity Indicator

In the present invention, the phosphorus cycle activity indicator is an indicator for analyzing the relation between soil bacteria and the activity of conversion of phosphorus-containing organic compounds into phosphoric acid, i.e., the activity of conversion of phosphorus compounds that cannot be used by plants into phosphoric acid that can be used by plants.

The phosphorus cycle activity indicator in the present invention is represented as a value calculated using
(B-1) the soil bacteria count in target soil,
(B-2) the activity of forming phosphoric acid from phytic acid in the target soil, and
(B-3) the activity of forming phosphoric acid from compost in the target soil.

Phosphorus which is one of three major nutrients for plants closely relates to growth of plants, and thus evaluation of the phosphorus cycle activity is considered to be important for soil diagnosis.

In addition, plants absorb water-soluble phosphoric acid. Thus, it is considered that, in the case of soil having a large amount of water-soluble phosphoric acid therein, plants are more likely to absorb phosphorus.

Accordingly, the activity of conversion of a phosphorus compound into water-soluble phosphoric acid is considered to be an important factor for the phosphorus cycle activity.

In addition, as the phosphorus compound, phytic acid and compost are considered to be important in particular.

The phytic acid is a substance used by plants for storing phosphorus, and weeds and residues of postharvest agricultural crops contain a large amount of phytic acid. If microorganisms in the target soil have higher activity of releasing phosphoric acid from phytin contained in plant bodies, it can be judged that the soil has high quality.

In addition, compost is used as a means for externally supplying phosphorus to low-phosphorus soil. However, compost does not contain water-soluble phosphoric acid, but contains phosphoric acid as a component of bark compost, for example. If microorganisms in the target soil have higher activity of generating phosphoric acid from compost, it can be judged that the soil has high quality.

(B-1) Soil Bacteria Count

The soil bacteria count in the target soil is as per that described in above (IV) cycle activity indicator.

(B-2) Activity of Forming Phosphoric Acid from Phytic Acid

The activity of forming phosphoric acid from phytic acid in the target soil is as per that described in above (II) cycle activity indicator.

(B-3) Activity of Forming Phosphoric Acid from Compost

In the present invention, the activity of forming phosphoric acid from compost in the target soil represents a value indicating the activity of conversion of compost administered into the target soil into phosphoric acid, in other words, the activity of converting/decomposing compost so as to release water-soluble phosphoric acid.

Examples of compost include: plant compost such as bark compost; livestock compost such as poultry manure compost, cow manure compost, and swine manure compost; and seaweed compost. These types of compost may be used individually, or two or more types of compost may be used in combination.

Among these types of compost, the bark compost contains a large amount of phosphoric acid in the form of phytic acid or the like, and thus enables more appropriate evaluation. Normally, the content of total phosphoric acid ($P_2O_5$) in bark compost is 0.5% or more (dry matter content).

In addition, the manner in which compost is administered is not limited. Compost mixed with culture soil may be used. In this case, the mixing rate of the compost with respect to the total culture soil is about 10 to 50% in weight, and preferably about 25 to 35%.

Specifically, the activity of forming phosphoric acid from compost can be calculated as a value obtained from the following formula, when compost is administered into the target soil.

$$\text{Activity of forming phosphoric acid from compost } (\%) = [(P^6 - P^5)/P^4] \times 100$$

(In the formula, $P^4$ represents the amount of phosphoric acid in compost, $P^5$ represents the amount of water-soluble phosphoric acid on a compost administration day, and $P^6$ represents the amount of water-soluble phosphoric acid after a predetermined period of time following the compost administration.)

The amount of phosphoric acid in the compost can be measured using publicly known methods of determination of phosphoric acid content. For example, organic substances in compost are decomposed using perchloric acid, and extracted using 0.002 N sulfuric acid. The resultant substances are subjected to a molybdenum blue method, whereby the amount of total phosphoric acid is determined.

The compost administration day means a day on which compost is administered into the target soil. The amount of water-soluble phosphoric acid on the day on which compost is administered can be represented as the amount of water-soluble phosphoric acid on Day 0 of administration.

In addition, the predetermined period of time after the compost administration means a day after a predetermined period of time elapsed from the administration of compost into the target soil. For example, the amount of water-soluble phosphoric acid after three days has elapsed from the administration of compost into the target soil can be represented as the amount of water-soluble phosphoric acid on Day 3 of administration.

The length of the predetermined period of time can be set as appropriate, and is preferably three to seven days, and more preferably three days after administration. If the period of time is shorter or extremely longer than this, it is difficult to recognize difference in the activity.

In other words, as the activity of forming phosphoric acid from compost in the target soil, a value obtained from the following formula:

[Formula 5]

$$\text{Activity of forming phosphoric acid from compost}(\%) = \left( \frac{\text{amount of water soluble phosphoric acid on Day 3} - \text{amount of water soluble phosphoric acid on Day 0}}{\text{amount of phosphoric acid in compost}} \right) \times 100$$

is preferably used.

The amount of water-soluble phosphoric acid means, as described above, the amount of water-soluble phosphoric acid per unit dry weight of target soil, and can be measured in the same manner as that in the description above.

The activity of forming phosphoric acid from compost reflects conversion efficiency from compost to water-soluble phosphoric acid. It is considered that if the activity is higher, phosphorus in compost is more likely to be used. Accordingly, it is considered that if the activity is higher, the soil has excellent quality, and the amount of compost to be introduced can be minimized. On the other hand, it is considered that if the activity is lower, phosphorus in compost is less likely to be used. Accordingly, it is considered that, if the activity is lower, the soil has insufficient quality, and consequently it is necessary to increase the amount of compost to be introduced, or to introduce phosphorus fertilizer.

(B-4) Evaluation of Phosphorus Cycle Activity

Above-described (B-1), (B-2), and (B-3) are important factors for phosphorus cycle in soil, and combined analysis of these factors is a key for appropriate diagnosis.

If the following conditions are all satisfied in relation to (B-1), (B-2), and (B-3), it is judged that the soil has excellent phosphorus cycle activity, whereas if any of the following conditions is not satisfied, it is judged that the soil does not have excellent phosphorus cycle activity.

Regarding the reference value of the soil bacteria count, $3.25 \times 10^9$ cells/g-soil which is the average value of the soil bacteria count in agricultural land soil is used as 100% of the reference value. When a measured value is 10% or more, preferably 40% or more, it can be evaluated that the soil has a sufficient soil bacteria count.

The reference value of the activity of forming phosphoric acid from phytic acid can be set as follows. That is, phytic acid is administered into the target soil at 1% (w/w) per unit dry weight of target soil, and the amount of water-soluble phosphoric acid on Day 0 and the amount of water-soluble phosphoric acid on Day 3 are measured. When a value obtained using the above formula is 100%, the value can be set as the reference value. If a measured value is 10% or more, preferably 30% or more, it can be evaluated that the soil has excellent activity of forming phosphoric acid from phytic acid.

The reference value of the activity of forming phosphoric acid from compost can be set as follows. That is, compost is administered into the target soil at 1% (w/w) per unit dry weight of target soil, and the amount of water-soluble phosphoric acid on Day 0 and the amount of water-soluble phosphoric acid on Day 3 are measured. When a value obtained using the above formula is 100%, the value can be set as the reference value. If a measured value is 10% or more, preferably 30% or more, it can be evaluated that the soil has excellent activity of forming phosphoric acid from compost.

Although a method of calculating the phosphorus cycle activity indicator through combination of the above-described factors (B-1), (B-2), and (B-3) is not particularly limited, it is preferable to calculate the phosphorus cycle activity indicator as follows. That is, an equilateral triangle is formed with the preset reference value of the soil bacteria count, the preset reference value of the activity of forming phosphoric acid from phytic acid, and the preset reference value of the activity of forming phosphoric acid from compost set as the vertices, whereas a triangle is formed with points of measured values of (B-1) the soil bacteria count, (B-2) the activity of forming phosphoric acid from phytic acid, and (B=3) the activity of forming phosphoric acid from compost set as the vertices, the points being located on line segments extending from the center of gravity of the equilateral triangle to the corresponding vertices. The proportion of the area of the triangle with respect to that of the equilateral triangle is calculated as the cycle activity indicator.

Accordingly, comprehensive evaluation or judgment based on the factors (B-1), (B-2), and (B-3) can be made easily. Further, as illustrated in FIG. 4, due to diagrammatic representation, the size of the indicator can be understood at a glance. Still further, which of the variables (B-1) to (B-3) needs to be improved is easily understandable.

In this case, if the above conditions relating to (B-1), (B-2), and (B-3) are all satisfied; and the proportion of the area of the triangle formed with the measured points as the vertices with respect to the area of the equilateral triangle formed with the reference values as the vertices is 1 or more, preferably 10 or more, then it can be judged that the soil has excellent phosphorus cycle activity. On the other hand, if the above values are not satisfied, it can be judged that the soil does not have excellent phosphorus cycle activity.

The phosphorus cycle activity indicator can be calculated using a calculation method described in the examples herein, more specifically.

If the phosphorus cycle activity indicator is higher, it can be evaluated that plants are more likely to absorb phosphorus components, and that the efficiency in phosphorus cycle in soil is preferable.

(C) Potassium Cycle Activity Indicator

In the present invention, the potassium cycle activity indicator is an indicator for analyzing the relation between conversion of potassium-containing compounds and soil bacteria.

The potassium cycle activity indicator in the present invention is represented as a value calculated using
(C-1) the soil bacteria count in target soil,
(C-2) the potassium release rate in the target soil, and
(C-3) the activity of forming potassium from compost in the target soil.

Potassium which is one of three major nutrients for plants is considered to closely relate to growth of plants, and thus evaluation of the potassium cycle activity is considered to be important for soil diagnosis.

Vegetables absorb potassium released in soil, and thus it is considered that the amount of free potassium in soil is an important factor for the potassium cycle activity.

In addition, compost is used as a means for externally supplying potassium to low-potassium soil. In compost, potassium is contained in remains of animals and plants in large amounts. However, potassium that plants can use is free potassium. Thus, it is considered that the activity of microorganisms' converting potassium contained in compost into free potassium is an important factor.

(C-1) Soil Bacteria Count

The soil bacteria count in the target soil is as per that described in above (IV) cycle activity indicator.

(C-2) Potassium Release Rate

In the present invention, the potassium release rate in the target soil is a value indicating the amount of potassium per unit dry weight of target soil.

Specifically, the potassium release rate in the target soil is a value calculated using the following formula.

Potassium release rate(%)=[($K^3-K^2$)/$K^1$]×100

(In the formula, $K^1$ represents the amount of potassium in the target soil on the measurement starting day, $K^2$ represents the amount of potassium release on a measurement starting day, and $K^3$ represents the amount of potassium release after a predetermined period of time following the measurement starting day.)

The amount of potassium in the target soil can be determined using publicly known methods, and may be obtained, as follows. For example, an ammonium acetate aqueous solution is added to soil, followed by filtration to obtain filtrate. From the obtained filtrate, which is a potassium extraction liquid, the amount of potassium is measured using an atomic absorption spectrophotometer.

The amount of potassium release means the amount of potassium per unit dry weight of target soil.

The amount of potassium release can be measured using atomic absorption spectrophotometry or ICP-MS. For example, potassium released in soil is extracted using distilled water, and the extracted liquid is measured using an atomic absorption spectrophotometer, whereby the amount of potassium release can be obtained. Specifically, the amount of potassium in soil can be measured using a method of determination of the amount of potassium, which uses an atomic absorption spectrophotometer, described in the examples herein.

Preferably, as the potassium release rate, a value obtained from the following formula:

$$\text{Potassium release rate}(\%) = \left( \frac{\text{amount of potassium release on Day 3} - \text{amount of potassium release on Day 0}}{\text{amount of potassium in target soil}} \right) \times 100 \quad \text{[Formula 6]}$$

can be preferably used.

The potassium release rate reflects the amount of potassium usable by plants. It is considered that if the value is greater, potassium in soil is more likely to be used. Accordingly, it is considered that if the value is greater, the soil has excellent quality, and the amount of potassium to be introduced externally can be minimized.

On the other hand, it is considered that if the value is lower, potassium in soil is less likely to be used. Accordingly, if the value is lower, it is diagnosed that the soil has insufficient quality, and consequently it is necessary to increase the amount of potassium to be introduced externally.

(C-3) Activity of Forming Potassium from Compost

The activity of forming potassium from compost in target soil is as per that described in above (III) cycle activity indicator.

(C-4) Evaluation of Potassium Cycle Activity

Above-described (C-1), (C-2), and (C-3) are important factors for potassium cycle in soil, and combined analysis of these factors is a key for appropriate soil diagnosis.

If the following conditions are all satisfied in relation to (C-1), (C-2), and (C-3), it is judged that the soil has excellent potassium cycle activity, whereas if any of the following conditions is not satisfied, it is judged that the soil does not have excellent potassium cycle activity.

Regarding the reference value of the soil bacteria count, $3.25 \times 10^9$ cells/g-soil which is the average value of the soil bacteria count in agricultural land soil is used as 100% of the reference value. When a measured value is 10% or more, preferably 40% or more, it can be evaluated that the soil has a sufficient soil bacteria count.

Regarding the reference value of the potassium release rate, the activity of conversion of potassium in the target soil into free potassium completely in three days is defined as 100%. When a measured value is 5% or more, preferably 10% or more, it can be evaluated that the soil has sufficient potassium release rate.

The reference value of the activity of forming potassium from compost can be set as follows. That is, compost is administered into the target soil at 1% (w/w) per unit dry weight of target soil, and the amount of potassium release on Day 0 and the amount of potassium release on Day 3 are measured. When a value obtained using the above formula is 100%, the value can be set as the reference value. If a measured value is 5% or more, preferably 20% or more, it can be evaluated that the soil has excellent activity of forming potassium from compost.

Although a method of calculating a potassium cycle activity indicator through combination of the above-described factors (C-1), (C-2), and (C-3) is not particularly limited, it is preferable to calculate the potassium cycle activity indicator as follows. That is, an equilateral triangle is formed with the preset reference value of the soil bacteria count, the preset reference value of the amount of potassium release, and the preset reference value of the activity of forming potassium from compost set as the vertices, whereas a triangle is formed with points of measured values of (C-1) the soil bacteria count, (C-2) the amount of potassium release, and (C-3) the activity of forming potassium from compost set as the vertices, the points being located on line segments extending from the center of gravity of the equilateral triangle to the corresponding vertices. The proportion of the area of the triangle with respect to that of the equilateral triangle is calculated as the potassium cycle activity indicator.

Accordingly, comprehensive evaluation or judgment based on the factors (C-1), (C-2), and (C-3) can be made easily. Further, as illustrated in FIG. 5, due to diagrammatic representation, the size of the indicator can be understood at a glance. Still further, which of the variables (C-1) to (C-3) needs to be improved is easily understandable.

In this case, if the above conditions relating to (C-1), (C-2), and (C-3) are all satisfied; and the proportion of the area of the triangle formed with the measured points as the vertices with respect to the area of the equilateral triangle formed with the reference values as the vertices, is 1 or more, preferably 5 or more, then it can be judged that the soil has excellent potassium cycle activity. On the other hand, if any of the above values is not satisfied, it can be judged that the soil does not have excellent potassium cycle activity.

The potassium cycle activity indicator can be calculated using a calculation method described in the examples herein, more specifically.

If the potassium cycle activity indicator is higher, it can be evaluated that plants are more likely to absorb potassium components, and that the efficiency in potassium cycle in the soil is preferable.

1.3. Target Soil

In the present invention, the type of target soil is not particularly limited. Examples of the target soil include agricultural land, soil having been subjected to bioremediation treatment, and the like.

For example, the present invention can be used as an agricultural land diagnosis method for diagnosing whether the quality of agricultural land is suitable for vegetation, or whether the agricultural land needs to be improved so as to be suitable for vegetation. In addition, the present invention can be used as a purified soil diagnosis method for judging that in soil having been subjected to bioremediation treatment, whether substance cycle activities by soil microorganisms are recovered, and whether the soil can be used for normal purposes.

1.4. Diagnosis

In the present invention, soil diagnosis is performed using the above-described cycle activity indicator, or (A) the nitrogen cycle activity indicator, (B) the phosphorus cycle activity indicator, and (C) the potassium cycle activity indicator.

For the soil diagnosis, other indicators than the above-described cycle activity indicator or the indicators (A) to (C) may be used. Examples of other indicators include pH, electrical conductivity, dissolved oxygen concentration, grain size, and porosity of soil. These indicators can be measured using publicly known methods.

Further, indicators for other components, such as an indicator relating to carbon may be added for diagnosis. As the indicator relating to carbon, total organic carbon (TOC) may be used as the indicator. In order for microorganisms to have various activities (nitrogen cycle activity and the like), carbon sources as living components and energy source to maintain activities are necessary. Thus, the amount of carbon is also considered to be an important factor.

Further, publicly known indicators relating to soil or compost, such as a ratio of total organic carbon to total nitrogen (C/N ratio), may be used.

A method of using the above indicators (A) to (C) for diagnosis is not particularly limited. For example, diagnosis may be performed by obtaining a sum or product of the indicators (A) to (C), or an operation value of the indicators (A) to (C) as a comprehensive indicator. For example, if the sum of the indicators (A) to (C) relating to soil is greater, it can be diagnosed that the soil has high quality and is suitable for vegetation.

For example, as described above, an equilateral triangle is formed with the reference values set as the vertices, whereas a triangle is formed with points of measured values set as the vertices. The proportion of the area of the triangle with respect to that of each equilateral triangle is calculated as each of the indicators (A) to (C), and the average of the proportions is calculated. If the average is 10 or more, preferably 35 or more, it can be judged that the soil is suitable for vegetation, whereas if the above values are not satisfied, it can be judged that the soil is not suitable for vegetation.

Further, as described above, an equilateral triangle is formed with the reference values set as the vertices, whereas a triangle is formed with points of measured values set as the vertices. The proportion of the area of the triangle with respect to that of each equilateral triangle is calculated as each of the indicators (A) to (C). With respect to an equilateral triangle having vertices each set as 100, a triangle is formed with vertices which indicate the above-described proportions and located on line segments extending from the center of gravity of the equilateral triangle to the corresponding vertices. When the proportion of the area of thus formed triangle with respect to the equilateral triangle is 1 or more, preferably 5 or more, it can be judged that the soil is suitable for vegetation, whereas if the above values are not satisfied, it can be judged that the soil is not suitable for vegetation.

In the case of judgment using the above-described methods, all the variables (A-1) to (A-3), (B-1) to (B-3), and (C-1) to (C-3) should satisfy the above-described conditions.

In addition, the above-described cycle activity indicator, or the indicators (A) to (C) may be diagnosed individually to judge which of nitrogen cycle, phosphorus cycle, and potassium cycle needs to be improved, and further to judge whether introduction of additional components is effective for improvement, or to determine whether improving the state of soil microorganisms is effective.

Further, soil diagnosis can be performed with the combined use of the indicators (A) to (C) and other indicators, as comprehensive indicators. Still further, diagnosis can be performed by reviewing the balance of the indicators (A) to (C) or comparing the indicators (A) to (C) to other indicators.

2. Soil Quality Control Method

According to the present invention, with the use of the above-described diagnosis method of the present invention, a soil quality control method is provided.

In the soil quality control method of the present invention, the above-described diagnosis method of the present invention is performed temporally, and temporal changes in the cycle activity indicator, (A) nitrogen cycle activity indicator, (B) phosphorus cycle activity indicator, and (C) potassium cycle activity indicator are analyzed, whereby soil quality is controlled.

A method of analyzing the temporal changes is not particularly limited, and any publicly known method can be used as appropriate. For example, analysis may be performed using values obtained by further converting or operating the indicators. Alternatively, analysis may be performed using display means such as suitable graphs or diagrams.

Further, analysis may be performed additionally using temporal change of other indicators than the above-described cycle activity indicator and the indicators (A) to (C).

Examples of other indicators include pH, electrical conductivity, dissolved oxygen concentration, grain size, and porosity of soil. Further, indicators for other nutrient components, such as total organic carbon are Included.

Further, by performing treatment necessary based on a result of analysis of the temporal changes, the quality of soil can be maintained. In particular, according to the present invention, it is possible to judge treatment relating to which of the components, nitrogen, phosphorus, and potassium is required.

Further, according to the quality control method of the present invention, not only the state of substances necessary for vegetation but also the state of microorganisms in soil can be understood. Accordingly, with the quality control method of the present invention, it is possible to understand whether the ecosystem in soil is favorably maintained through growth of plants, and whether cycle activities of various substances function properly.

3. Soil Improvement Method

According to the present invention, with the use of the above-described diagnosis method of the present invention, a soil quality improvement method is provided.

In the soil improvement method of the present invention, based on the above-described diagnosis method of the present invention, soil diagnosis results relating to the cycle activity indicator, (A) the nitrogen cycle activity indicator, (B) the phosphorus cycle activity indicator, and (C) the potassium cycle activity indicator are obtained. Through treatment in accordance with the details of the diagnosis, soil improvement is performed.

Details of the treatment include additional administration of fertilizer containing nitrogen, phosphorus, and/or potassium, administration of nutrient components for activating soil microorganisms, administration of microorganisms having cycle activities of nitrogen, phosphorus, and/or potassium, and the like. For example, if the ammonia reduction rate is low, ammonium oxidizing bacteria may be administered.

In the soil improvement method of the present invention, it is possible to judge treatment relating to which of the components, nitrogen, phosphorus, and potassium is required, and further, it is advantageously possible to determine the details of the treatment in consideration of the performance of soil microorganisms.

For example, even if it is understood that soil contains a large amount of nitrogen compounds, plants cannot sufficiently utilize nitrogen unless the activity of microorganisms converting the nitrogen compounds is sufficient. According to the present invention, it is possible to judge that treatment for enhancing the activity of microorganisms or administration of microorganisms having such an activity is effective for such circumstances. In addition, even if it is judged that the amount of nitrogen in soil is insufficient and that nitrogen needs to be introduced externally, the amount of nitrogen to be administered can be adjusted, and excessive administration of the nitrogen can be avoided as long as it is understood that the activity of microorganisms is sufficient.

In this manner, according to the soil improvement method of the present invention, with the effective use of the performance of the ecosystem in soil, soil improvement can be performed. Efficient soil improvement, and further efficient food production can be achieved.

Advantageous Effects of Invention

According to the present invention, it is possible to provide a soil diagnosis method which reflects cycle activities in soil, and in particular a soil diagnosis method which enables judgment of whether soil is suitable for cultivation of agricultural products.

The soil diagnosis method of the present invention reflects the state of microorganisms in soil which closely relates to substance cycles, and thus it is possible to accurately diagnose the quality of the agricultural land in accordance with the natural cycle system. In particular, with the diagnosis method of the present invention, it is possible to accurately diagnose the quality of soil that is suitable for farming methods using biomass, for example, which are free from chemical farming.

Further, according to the diagnosis method of the present invention, it is possible to judge which one of the nitrogen cycle, the phosphorus cycle, and potassium cycle, which are important for vegetation, needs to be improved. Still further, it is possible to judge the details of treatment for improvement, i.e., whether introduction of additional components is effective, or whether improvement of the state of soil microorganisms is effective.

Further, according to the quality control method of the present invention, the state of substance necessary for vegetation as well as the state of soil microorganisms can be understood. Accordingly, it is possible to understand whether the ecosystem in the soil is favorably maintained through growth of plants, and whether cycle activities of various substances function properly.

Further, according to the soil improvement method of the present invention, with the effective use of the performance of the ecosystem in soil, soil improvement can be performed. Efficient soil improvement, and further, improved profitability in agricultural production can be achieved.

As described above, the present invention provides a soil quality diagnosis method and a soil quality improvement method based on the natural cycle functions, and contributes to improvement in profitability of farming methods such as organic farming in which use of chemical substances is reduced, and establishment of an environmentally-sound agricultural production system.

DESCRIPTION OF EMBODIMENTS

Figure 1:
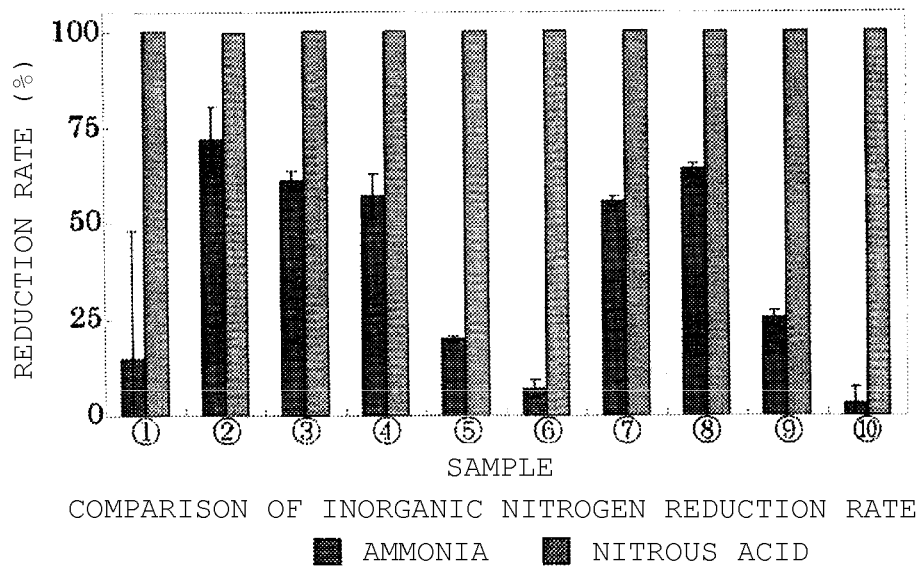
FIG. 1 is a diagram illustrating results of the ammonia reduction rate and the nitrous acid reduction rate in respective soil samples in examples. Each left bar indicates a value of the ammonia reduction rate, and each right bar indicates a value of the nitrous acid reduction rate.

Hereinafter, examples and test examples will be described for the sake of detailed description of the present invention. However, the present invention is not limited to these examples.

EXAMPLES

1. Development of Nitrogen Cycle Activity Analysis Method (1-1) Experimental Method 1a) Evaluation of Nitrification Ability Soil 10 g was weighed out and poured into a glass petri dish. After drying for two hours at 110° C., the moisture content of the soil was calculated from decrease of the weight. Soil 15 g (dry weight) strained through a 2 mm mesh sieve was poured into a 50 ml UM sample bottle, and an ammonium sulfate solution (0.080 mM) or a potassium nitrite solution (0.16 mM) was added at an amount of 60 µg-N/g-dry soil. The soil was thoroughly stirred, and left to stand at 25° C., with the moisture content kept constant for three days.

1b) Extraction of Inorganic Nitrogen from Soil

Sample soil 2.0 g and a 1M potassium chloride solution 20 ml were added to a 50 ml centrifuge tube, followed by suspension, and the mixture was shaken at 100 rpm for an hour. After shaking, the mixture was centrifuged at 10,000 rpm for 5 minutes, and the supernatant liquid was used as an inorganic nitrogen extraction liquid.

1c) Determination of Amount of Ammonia Nitrogen Using Indophenol Method

An amount of 1.0 ml of the inorganic nitrogen extraction liquid extracted from the soil was dispensed into a 2.0 ml microtube, and 500 µl of a sodium hypochlorite solution described in table 1 was added thereto, followed by agitation. The mixture was then left to stand at room temperature for 5 minutes. After standing, 500 µl of a phenol-sodium nitroprusside solution described in table 2 was added to the mixture, followed by agitation, and the obtained mixture was left to stand at 30° C. for 60 minutes. After standing, the absorbance at 640 nm was measured. For absorbance measurement, a calibration curve was prepared using an ammonia nitrogen standard solution to obtain a relational expression, and the amount of ammonia nitrogen ($NH_4^+$—N) was measured using the relational expression.

TABLE 1

| Composition of sodium hypochlorite aqueous solution | |
|---|---|
| reagent | (/L) |
| sodium hypochlorite solution | 10.0 ml |
| sodium hydroxide | 15.0 g |

TABLE 2

| Composition of phenol-sodium nitroprusside solution | |
|---|---|
| reagent | (g/L) |
| phenol | 5.0 |
| sodium nitroprusside | 0.0250 |

1d) Determination of Amount of Nitrite Nitrogen Using Naphthyl Ethylenediamine Method An amount of 1.0 ml of the inorganic nitrogen extraction liquid extracted from the soil was dispensed into a 1.5 ml microtube, and 100 µl of a diazotization agent described in table 3 was added thereto, followed by agitation. The mixture was left to stand at room temperature for 5 minutes, and 100 µl of a coupling agent described in table 4 was added to the mixture. The mixture thus obtained was left to stand at room temperature for 20 minutes, and the absorbance at 540 nm was measured. The amount of nitrite nitrogen ($NO_2^-$—N) was measured based on the calibration curve prepared using the nitrite nitrogen standard solution.

TABLE 3

| Composition of diazotization agent | |
|---|---|
| reagent | (g/L) |
| 2.4M hydrochloric acid | 1000 ml |
| sulfonylamide | 0.500 g |

TABLE 4

| Composition of coupling agent | |
|---|---|
| reagent | (g/L) |
| 0.12M hydrochloric acid | 1000 ml |
| N-1-naphthyl ethylenediamine dihydrochloride | 0.300 g |

1e) Determination of Amount of Nitrate Nitrogen Using Brucine Sulfanilic Acid Method An amount of 800 µl of the inorganic nitrogen extraction liquid extracted from the soil and 400 µl of a brucine sulfanilic acid solution described in table 5 were dispensed into a test tube, and 4.0 ml of a sulfuric acid solution (sulfuric acid: water=20:3) was added thereto, followed by agitation. After the mixture was left to stand at a cool dark place for 40 minutes, the absorbance at 410 nm was measured. For absorbance measurement, a calibration curve was prepared using a nitrate nitrogen standard solution to obtain a relational expression, and the amount of nitrate nitrogen ($NO_3^-$—N) was measured using the relational expression.

TABLE 5

| Composition of brucine sulfanilic acid solution | |
|---|---|
| reagent | (g/L) |
| brucine n hydrate | 10.0 g |
| sulfanilic acid | 1.0 g |
| hydrochloric acid | 30.0 ml |

1f) Determination of Soil Bacteria Count Using Environmental DNA (eDNA) Analysis Method soil 1.0 g was weighed out and poured into a 50 ml centrifuge tube, and 8.0 ml of a DNA extraction buffer solution (pH 8.0) described in table 6 and 1.0 ml of a 20% (w/v) sodiumdodecyl-sulfate solution were added thereto. The mixture was agitated at 1,500 rpm at room temperature for 20 minutes. After agitation, an amount of 1.5 ml of the mixture was separated from the 50 ml centrifuge tube, and poured into a sterilized 1.5 ml microtube, followed by centrifugation at 8,000 rpm at 16° C. for 10 minutes. An amount of 700 µl of the aqueous layer of the mixture was separated and poured into another microtube, and 700 µl of chloroform-isoamyl alcohol (24:1, v/v) was added thereto, followed by mixing. The mixture was then centrifuged at 13,000 rpm at 16° C. for 10 minutes. After centrifugation, an amount of 500 µl of the aqueous layer was separated and poured into still another microtube, and 2-propanol 300 µl was added thereto, followed by gentle mixing. The mixture was centrifuged at 13,000 rpm at 16° C. for 15 minutes. After centrifugation, the supernatant liquid was removed from the mixture, and 500 µl of 70% (v/v) ethanol was added to the microtube, followed by centrifugation at 13,000 rpm at 16° C. for 5 minutes. After centrifugation, the supernatant liquid was removed, and the remaining mixture was dried under reduced pressure for 30 minutes using an aspirator. An amount of 50 µl of a TE (10:1) buffer solution (pH 8.0), which is described in table 7, was added to solve the dried mixture thoroughly, and the resultant solution was used as an eDNA solution. Distilled water was added to 2.0 g of agarose, 4.0 ml of a 50×TAE buffer solution (pH 8.0) which is described in table 8, and 20 µl of a 0.1 mM ethidium bromide solution so as to be 200 ml, and 1.0% agarose gel was prepared. Loading Dye (Toyobo, Osaka) 1.0 µl was mixed with 5.0 µl of the eDNA solution to be a total amount of 6.0 µl. The mixture and 1.5 µl of Smart Ladder (Nippon Gene, Toyama) which includes a given amount of DNA were applied to the agarose gel. After being subjected to electrophoresis at 100 V for 40 minutes, the agarose gel was irradiated with UV for checking the DNA bands. With the use of KODAK 1D Image Analysis software (KODAK, NY, USA), DNA bands of the Smart Ladder were analyzed, and a calibration curve representing the amount of DNA versus fluorescence intensity was prepared. With the use of the calibration curve, the amounts of DNA in respective sample DNA solutions were obtained from the fluorescence intensity of the respective DNA bands, and the amount of eDNA per 1.0 g soil was calculated for each sample. Based on a calibration curve representing conversion of the amount of eDNA into soil bacteria count using DAPI staining, the soil bacteria count was obtained. From the determined amount of eDNA, and with the use of the following relational expression, the soil bacteria count was calculated.

$$Y = 1.7 \times 10^8 \times X \; (R^2 = 0.96)$$

[Y; soil bacteria count (cells/g-soil), X; amount of eDNA (µg/g-soil)]

TABLE 6

| Composition of DNA extraction buffer solution (pH 8.0) | |
| --- | --- |
| reagent | (g/L) |
| trishydroxymethylaminomethane | 12.1 |
| ethylenediaminetetraacetic acid, disodium salt | 37.2 |
| sodium dihydrogen phosphate | 12.0 |
| sodium chloride | 87.7 |
| hexadecyl methyl ammonium bromide | 10.0 |

TABLE 7

| Composition of TE 10:1 buffer solution (pH 8.0) | |
| --- | --- |
| reagent | (g/L) |
| trishydroxymethylaminomethane | 1.2 |
| ethylenediaminetetraacetic acid, disodium salt | 0.370 |

TABLE 8

| Composition of 50 × TAE buffer solution (pH 8.0) | |
| --- | --- |
| reagent | (g/L) |
| trishydroxymethylaminomethane | 108 |
| ethylenediaminetetraacetic acid, disodium salt | 18.6 |
| acetic acid | 57.0 |

(1-2) Measurement of Nitrification Ability

With 10 soil samples (No. 1 to 10) whose purposes and fertilization statuses differ from one another, the amount of ammonia nitrogen and the amount of nitrite nitrogen were measured as an amount of inorganic nitrogen in accordance with above 1b) to 1d), and thereby nitrification activity in the soil was analyzed. Table 9 shows the amount of inorganic nitrogen and the reduction rate of the inorganic nitrogen on Day 0 and on Day 3 after each sample was left to stand.

TABLE 9

Analysis example of inorganic nitrogen amount in soil sample on Day 0 and Day 3 after being left to stand

| sample No. | | (1) amount of inorganic nitrogen (µg-N/g-dry soil) | | | (2) amount of inorganic nitrogen (µg-N/g-dry soil) | |
| --- | --- | --- | --- | --- | --- | --- |
| | | ammonia | nitrous acid | | ammonia | nitrous acid |
| 1 | Day 0 | 50.5 ± 15.2 | 0 ± 0 | Day 0 | 45.8 ± 4.8 | 55.9 ± 1.0 |
| | Day 3 | 46.1 ± 31.4 | 0 ± 0 | Day 3 | 33.9 ± 12.3 | 0 ± 0 |
| | change amount (a/c) | −4.3 ± 16.5 | 0 ± 0 | a/c | −11.9 ± 8.3 | −55.9 ± 1.0 |
| 2 | Day 0 | 59.4 ± 4.6 | 0.32 ± 0.01 | Day 0 | 1.40 ± 0.33 | 59.1 ± 0.8 |
| | Day 3 | 16.9 ± 6.4 | 0.33 ± 0.01 | Day 3 | 2.03 ± 2.00 | 0.2 ± 0.1 |
| | a/c | −42.5 ± 2.2 | 0.01 ± 0.01 | a/c | 0.63 ± 1.60 | −58.9 ± 0.8 |
| 3 | Day 0 | 61.4 ± 0.9 | 0.01 ± 0.02 | Day 0 | 1.24 ± 0.90 | 63.1 ± 0.8 |
| | Day 3 | 24.0 ± 2.1 | 0.12 ± 0.03 | Day 3 | 3.00 ± 2.10 | 0.1 ± 0 |
| | a/c | −37.4 ± 1.2 | 0.11 ± 0.03 | a/c | 1.76 ± 0.28 | −63.0 ± 0.8 |

TABLE 9-continued

Analysis example of inorganic nitrogen amount in soil sample on Day 0 and Day 3 after being left to stand

| sample No. | | (1) amount of inorganic nitrogen (μg-N/g-dry soil) | | | (2) amount of inorganic nitrogen (μg-N/g-dry soil) | |
|---|---|---|---|---|---|---|
| | | ammonia | nitrous acid | | ammonia | nitrous acid |
| 4 | Day 0 | 53.7 + 1.9 | 0 ± 0 | Day 0 | 1.24 ± 0.91 | 54.7 ± 2.1 |
| | Day 3 | 23.0 ± 3.7 | 0.08 ± 0.09 | Day 3 | 0.34 ± 0.48 | 0 ± 0 |
| | a/c | −30.7 ± 2.5 | 0.08 ± 0.09 | a/c | −0.90 ± 1.38 | −54.7 ± 2.1 |
| 5 | Day 0 | 66.9 ± 2.2 | 0 ± 0 | Day 0 | 1.76 ± 3.05 | 56.3 ± 1.0 |
| | Day 3 | 53.7 ± 1.6 | 0.01 ± 0.01 | Day 3 | 2.57 ± 1.51 | 0 ± 0 |
| | a/c | −13.2 ± 0.8 | 0.01 ± 0.01 | a/c | 0.81 ± 1.66 | −56.3 ± 1.0 |
| 6 | Day 0 | 54.6 ± 4.9 | 0.02 ± 0.01 | Day 0 | 2.4 ± 2.67 | 62.7 ± 0.2 |
| | Day 3 | 50.7 ± 3.4 | 0.01 ± 0.01 | Day 3 | 0.06 ± 0.1 | 0 ± 0 |
| | a/c | −3.9 ± 1.6 | −0.01 ± 0.01 | a/c | −2.34 ± 2.74 | −62.7 ± 0.2 |
| 7 | Day 0 | 58.1 ± 0.5 | 1.12 ± 0.49 | Day 0 | 1.12 ± 0.49 | 66.5 ± 1.7 |
| | Day 3 | 25.6 ± 1.0 | 0 ± 0 | Day 3 | 0 ± 0 | 0 ± 0 |
| | a/c | −32.4 ± 0.6 | −1.12 ± 0.49 | a/c | −1.12 ± 0.49 | −66.5 ± 1.7 |
| 8 | Day 0 | 56.8 ± 3.7 | 0.24 ± 0.04 | Day 0 | 2.20 ± 0.47 | 49.9 ± 6.4 |
| | Day 3 | 20.3 ± 0.4 | 0.01 ± 0.01 | Day 3 | 0 ± 0 | 0.1 ± 0 |
| | a/c | −36.5 ± 3.2 | −0.23 ± 0.05 | a/c | −2.20 ± 0.47 | −49.8 ± 6.5 |
| 9 | Day 0 | 52.2 ± 1.3 | 0.01 ± 0.02 | Day 0 | 0 ± 0 | 63.6 ± 0.9 |
| | Day 3 | 39.0 ± 0.9 | 0 ± 0 | Day 3 | 0.01 ± 0.12 | 0 ± 0 |
| | a/c | −13.2 ± 1.2 | −0.01 ± 0.02 | a/c | 0.01 ± 0.12 | −63.6 ± 0.9 |
| 10 | Day 0 | 57.6 ± 2.9 | 0.04 ± 0.02 | Day 0 | 1.66 ± 0.42 | 57.1 ± 0.8 |
| | Day 3 | 55.8 ± 3.9 | 0.24 ± 0.03 | Day 3 | 0.69 ± 1.12 | 0 ± 0 |
| | a/c | −1.8 ± 2.5 | 0.20 ± 0.02 | a/c | −0.97 ± 1.43 | −57.1 ± 0.8 |

In experiment (1), ammonium sulfate solution was added at an amount of 60 μg-N/g-dry soil.
In experiment (2), potassium nitrite solution was added at an amount of 60 μg-N/g-dry soil.
An amount of inorganic nitrogen was obtained by subtracting a control value from an actual measured value.

For the sake of further analysis of the nitrification activity in each sample, the ammonia reduction rate and the nitrous acid reduction rate were calculated from the reduction amount of the inorganic nitrogen.

The ammonia reduction rate was calculated from the amount of ammonia nitrogen measured in accordance with above 1b) and 1c), using the following formula.

$$\text{Ammonia reduction rate}(\%) = \left(1 - \frac{\text{amount of ammonia nitrogen on Day 3}}{\text{amount of ammonia nitrogen on Day 0}}\right) \times 100 \quad [\text{Formula 7}]$$

The nitrous acid reduction rate was calculated from the amount of nitrite nitrogen ($NO_2^-$—N) measured in accordance with above b) and d), using the following formula.

$$\text{Nitrous acid reduction rate}(\%) = \left(1 - \frac{\text{amount of nitrite nitrogen on Day 3}}{\text{amount of nitrite nitrogen on Day 0}}\right) \times 100 \quad [\text{Formula 8}]$$

FIG. 1 illustrates the results of the ammonia reduction rate and the nitrous acid reduction rate in each sample.

The nitrous acid reduction rate in all the samples measured substantially 100%. The ammonia reduction rate, on the other hand, varied depending on the samples, ranging from 72.0% at the highest to 3.10% at the lowest. Since the ammonia reduction rate was lower than the nitrous acid reduction rate with respect to all the samples, it was considered that reaction from ammonia to nitrous acid is rate-limiting in terms of nitrification reaction.

Accordingly, it was indicated that the above-described evaluation method is applicable to analysis of soil which contains fertilizer in large amounts.

(1-3) Analysis of Soil Bacteria Count

It is considered that soil bacteria closely relates to substance cycles. Thus, the soil bacteria count in each sample was analyzed using the above method 1f. In addition, the average value of the soil bacteria count in agricultural land soil in the database, i.e., $3.25 \times 10^9$ cells/g-soil was set as 100, and the measured soil bacteria count was calculated as the relative value (hereinafter also referred to as bacteria amount). Table 10 shows the soil bacteria count and the bacteria amount, in each sample.

TABLE 10

Soil bacteria count and bacteria amount in sample

| sample No. | soil bacteria count ($\times 10^8$ cells/g-soil) | bacteria amount (%) |
|---|---|---|
| 1 | 9.91 ± 0.62 | 30.5 |
| 2 | 9.12 ± 0.07 | 28.1 |
| 3 | 5.89 ± 0.47 | 18.1 |
| 4 | 4.32 ± 0.16 | 13.3 |
| 5 | 3.65 ± 0.28 | 11.2 |
| 6 | 3.01 ± 0.22 | 9.26 |
| 7 | 2.26 ± 0.62 | 6.95 |
| 8 | 2.12 ± 0.18 | 6.52 |
| 9 | 1.86 ± 0.22 | 5.72 |
| 10 | N.D. | 0 |

*N.D.: less than detection limit ($0.78 \times 10^7$ cells/g-soil)

(1-4) Analysis of Nitrogen Cycle Activity

Figure 2:
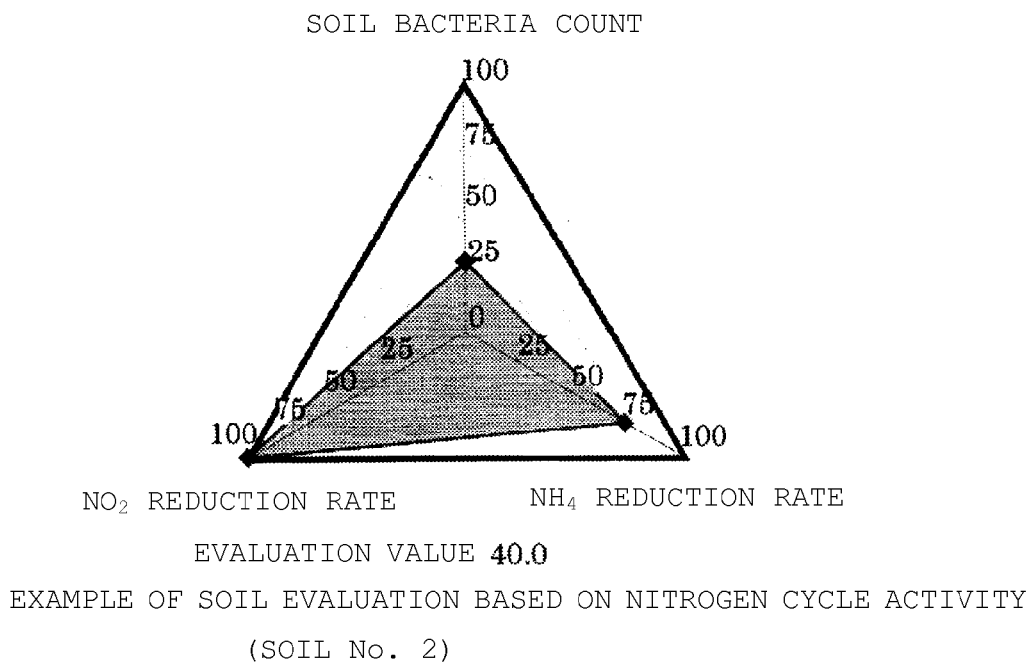
FIG. 2 is a diagram illustrating an example of evaluation of nitrogen cycle activity for which soil bacteria count, ammonia reduction rate, and nitrous acid reduction rate are used.

Based on the obtained three items, i.e., the soil bacteria count, the ammonia reduction rate, and the nitrous acid reduction rate, a chart as shown in FIG. 2 was prepared for evaluation of nitrogen cycle activity in soil.

In FIG. 2, the soil bacteria count indicates the proportion of the soil bacteria count in each sample in the case where the average value of the soil bacteria count in agricultural land soil, i.e., $3.25 \times 10^9$ cells/g-soil is set as 100, and namely indicates the bacteria amount.

Further, the ammonia reduction rate indicates the proportion of the ammonia reduction rate in each sample in the case where the activity of reducing ammonia compounds 60 µg-N/g-dry soil by 100% in three days is set as 100.

Further, the nitrous acid reduction rate indicates the proportion of the nitrous acid reduction rate in each sample in the case where the activity of reducing nitrous acid compounds 60 µg-N/g-dry soil by 100% in three days is set as 100.

Still further, in the chart, the area of the triangle whose vertices represent 100 was set as 100, and the relative value of the area of the internal triangle was calculated as a nitrogen cycle indicator for each sample. Table 11 shows the nitrogen cycle indicator for each sample.

TABLE 11

Evaluation value of nitrogen cycle activity in each sample

| sample No. | evaluation value |
| --- | --- |
| 1 | 16.6 |
| 2 | 40.0 |
| 3 | 30.0 |
| 4 | 26.0 |
| 5 | 11.0 |
| 6 | 5.70 |
| 7 | 22.2 |
| 8 | 24.9 |
| 9 | 10.8 |
| 10 | 1.00 |

As indicated in Table 11 and FIG. 2, regarding sample No. 2, the ammonia reduction rate, the nitrous acid reduction rate, and the bacteria amount were relatively high, and thus it is considered that if organic nitrogen is added to the soil, the nitrogen is quickly converted into ammonia, and also oxidized into nitric acid.

(1-5) Improvement in Nitrogen Cycle Activity by Administration of Autotrophic Ammonium Oxidizing Bacteria into Soil For soil having poor nitrification activity, that is, poor nitrogen cycle activity, administration of microorganisms which oxidize ammonia is considered to be effective. Accordingly, whether administration of ammonium oxidizing bacteria facilitates nitrification activity was analyzed.

Two types of autotrophic ammonium oxidizing bacteria (strain A, strain B) were administered into soil to study whether nitrification activity was facilitated.

Figure 3:
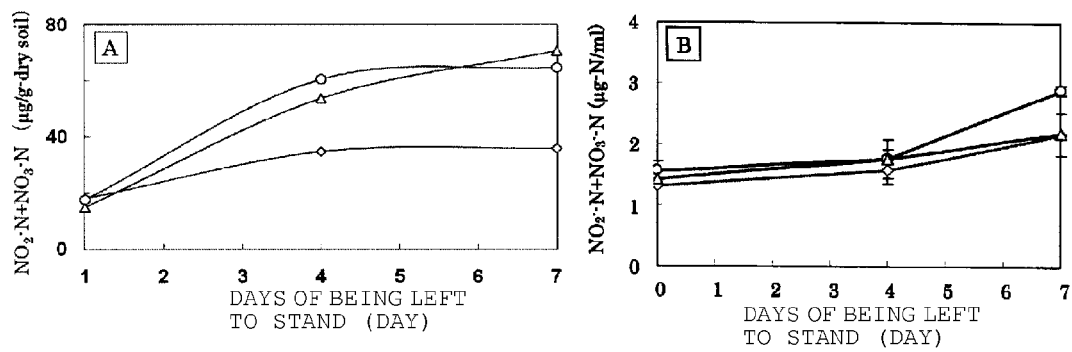
FIG. 3 is a diagram illustrating results of analysis, in the examples, on how administration of autotrophic ammonium oxidizing bacteria affects the nitrogen cycle activity in soil. FIG. A represents soil No. 1, and FIG. B represents soil No. 2. In addition, ◇ indicates a case of inoculation of no strain; ○ indicates a case of administration of strain A; and △ indicates a case of administration of strain B.

A culture medium of strain A or strain B was concentrated by centrifugation, and administered into sterilized soil (soil 1 and 2) at an amount of $1.0 \times 10^7$ cells/g-dry soil. Further, ammonia nitrogen was administered into the soil at an amount of 60 µ-N/g dry soil, and the mixture was left to stand for 3 days. The temporal change of the amount of inorganic nitrogen was analyzed. The results are shown in FIG. 3. FIG. 3 illustrates the temporal change of the amount of nitrite nitrogen and that of the amount of the nitrate nitrogen.

As illustrated in FIG. 3, in the case where autotrophic ammonium oxidizing bacteria were administered, the accumulated amount of nitrite nitrogen and that of nitrate nitrogen were increased as compared to the case where they were not administered.

Accordingly, it was indicated that administration of autotrophic ammonium oxidizing bacteria into soil facilitates the nitrogen cycle activity.

2. Analysis of Phosphorus Cycle Activity

With 10 soil samples (No. 11 to 20) whose purposes and fertilization statuses differ from one another, the phosphorus cycle in the soil was analyzed.

(2-1) Experimental Method

2a) Analysis of Soil Bacteria Count

The soil bacteria count was determined using the same eDNA analysis method as above if).

2b) Analysis of Activity of Forming Phosphoric Acid from Phytic Acid

Sample soil 100 g was poured into a 250 ml UM sample bottle, and agitated thoroughly. An amount of 2.0 g of the soil was weighed out and poured into a 50 ml centrifuge tube, and distilled water 20 ml was added thereto, followed by shaking at 100 rpm for 60 minutes. The mixture was centrifuged at 10,000 rpm for 5 minutes, and the supernatant liquid was subjected to the molybdenum blue method as a water-soluble phosphoric acid extraction liquid. An amount of 1.0 ml of the water-soluble phosphoric acid extraction liquid was dispensed into a 1.5 ml microtube. An amount of 100 µl of a mixed solution of a molybdenum blue stock solution shown in table 12 and a 0.41M L(+)-ascorbic acid aqueous solution which are mixed at a ratio of 5:1 is added to the microtube, followed by agitation, and the mixture was left to stand at 30° C. for 30 minutes. After standing, the absorbance at 720 nm was measured. From a calibration curve prepared using a phosphoric acid standard solution, the amount of water-soluble phosphoric acid in the soil was determined, and was set as the amount of water-soluble phosphoric acid on Day 0.

Phytic acid was added to the sampled soil at an amount of 1% (w/w), followed by thorough agitation. The mixture was left to stand at room temperature for 3 days. An amount of 2.0 g of the soil was weighed out and poured into a 50 ml centrifuge tube, and water-soluble phosphoric acid was extracted using the above-described method. The extract was subjected to the molybdenum blue method, and the amount of water-soluble phosphoric acid was measured and set as the amount of water-soluble phosphoric acid on Day 3.

Further, based on the fact that 1 mol of phytic acid contains 6 molecules of phosphoric acid, the amount of phosphoric acid in phytic acid was calculated from the amount of phytic acid administered.

Based on the amount of water-soluble phosphoric acid and the amount of phosphoric acid in phytic acid thus obtained, the activity of forming phosphoric acid from phytic acid was calculated using the following formula.

[Formula 9]

$$\text{Activity of forming phosphoric acid from phytic acid}(\%) = \left( \frac{\text{amount of water soluble phosphoric acid on Day 3} - \text{amount of water soluble phosphoric acid on Day 0}}{\text{amount of phosphoric acid in phytic acid}} \right) \times 100$$

TABLE 12

Composition of molybdenum blue stock solution

| reagent | (/L) |
|---|---|
| hexaammonium heptamolybdate, tetrahydrate | 212 g |
| bis[(+)-tartrato]diantimonate(III) dipotassium trihydrate | 210.48 g |
| sulfuric acid (concentrated sulfuric acid:water = 2:1) | 240 ml |
| ammonium amidosulfate | 210 g |

2c) Analysis of Activity of Forming Phosphoric Acid from Compost

Sample soil 100 g was poured into a 250 ml UM sample bottle, and agitated thoroughly. An amount of 2.0 g of the soil was weighed out and poured into a 50 ml centrifuge tube, and distilled water 20 ml was added thereto, followed by shaking at 100 rpm for 60 minutes. The mixture was centrifuged at 10,000 rpm for 5 minutes, and extracted water-soluble phosphoric acid was subjected to the molybdenum blue method. The amount of the phosphoric acid was then determined, and was set as the amount of water-soluble phosphoric acid on Day 0.

Bark compost containing culture soil ("Hana-chan Baiyodo" (Hanagokoro, Nagoya)) was added to the sampled soil at an amount of 1% (w/w), followed by thorough agitation. The mixture was left to stand at room temperature for 3 days. An amount of 2.0 g of the soil was weighed out and poured-into a 50 ml centrifuge tube, and water-soluble phosphoric acid was extracted using the above-described method. The extract was subjected to the molybdenum blue method, and the amount of the water-soluble phosphoric acid was measured and set as the amount of water-soluble phosphoric acid on Day 3.

Further, organic substances in the compost was decomposed using perchloric acid, and extracted using 0.002 N sulfuric acid to be subjected to the molybdenum blue method. Then, the amount of phosphoric acid in the compost was measured.

Based on the amount of water-soluble phosphoric acid and the amount of phosphoric acid in the compost thus obtained, the activity of forming phosphoric acid from compost was calculated from the following formula.

[Formula 10]

$$\text{Activity of forming phosphoric acid from compost}(\%) = \left( \frac{\text{amount of water soluble phosphoric acid on Day 3} - \text{amount of water soluble phosphoric acid on Day 0}}{\text{amount of phosphoric acid in compost}} \right) \times 100$$

(2-2) Evaluation of Soil Based on Phosphorus Cycle and Soil Bacteria Count

Figure 4:
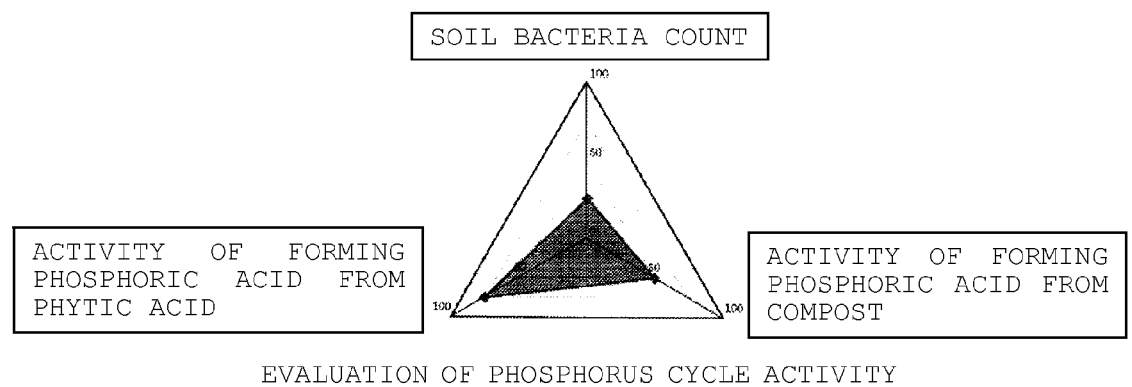
FIG. 4 is a diagram illustrating an example, of evaluation of phosphorus cycle activity for which soil bacteria count, activity of forming phosphoric acid from phytic acid, and activity of forming phosphoric acid from compost are used.

With the use of three items, i.e., the soil bacteria count, the activity of forming phosphoric acid from phytic acid, and the activity of forming phosphoric acid from compost, a chart as shown in FIG. 4 was prepared.

In FIG. 4, the soil bacteria count indicates the proportion of the soil bacteria count in each sample in the case where the average value of the soil bacteria count in agricultural land soil, i.e., $3.25 \times 10^9$ cells/g-soil is set as 100.

Further, the activity of forming phosphoric acid from phytic acid indicates the proportion of the activity of forming phosphoric acid from phytic acid in each sample in the case where the activity of completely converting phosphoric acid in phytic acid of an amount of 1% (w/w) into water-soluble phosphoric acid in three days is set as 100.

Further, the activity of forming phosphoric acid from compost indicates the proportion of the activity of forming phosphoric acid from compost in each sample in the case where the activity of completely converting phosphoric acid in compost of an amount of 1% (w/w) into water-soluble phosphoric acid in three days is set as 100.

Still further, in the chart, the area of the triangle whose vertices represent 100 was set as 100, and the relative value of the area of the internal triangle was calculated as a phosphorus cycle activity indicator for each sample. Table 13 shows the phosphorus cycle activity indicator for each sample.

TABLE 13

Evaluation value of phosphorus cycle activity in each sample

| sample No. | evaluation value |
|---|---|
| 11 | 90.1 |
| 12 | 100.00 |
| 13 | 31.1 |
| 14 | 37.3 |
| 15 | 40.9 |
| 16 | 39.7 |
| 17 | 39.1 |
| 18 | 63.4 |
| 19 | 48.2 |
| 20 | 00.8 |

The soil of sample No. 12 has a higher phosphorus cycle activity indicator, and it can be evaluated that plants are more likely to absorb and use phosphoric acid in the soil.

3. Structure of Potassium Cycle Activity Analysis Method

With 10 soil samples (No. 11 to 20) whose purposes and fertilization statuses differ from one another, the potassium, cycle in the soil was analyzed.

(3-1) Experimental Method

3a) Analysis of Soil Bacteria Count

The soil bacteria count was determined using the same eDNA analysis method as above 1f.

3b) Determination of Potassium Release Rate

Soil 3.0 g was weighed out and poured into a 50 ml conical flask, and 0.5 M nitric acid 40 ml was added thereto, followed by agitation for 60 minutes with a stirrer: After agitation, the mixture was filtered, and the filtrate was used as a potassium extraction liquid. The extraction liquid was measured using an atomic absorption spectrophotometer (Z-2300, Hitachi High-Technologies, Tokyo). Regarding the measurement conditions, acetylene and compressed air were used as fuel gas and supporting gas, respectively, and measurement was conducted while the pressure of each gas was set at 0.5 MPa. Based on a calibration curve prepared using a potassium standard solution, the amount of potassium release in the soil was determined, and set as the amount of potassium release on the measurement starting day (Day 0).

The amount of potassium release was determined in the same manner three days after start of measurement, and was set as the amount of potassium release on Day 3.

Further, soil 3.0 g taken on the same day as the measurement starting day was weighed out and poured into a 50 ml conical flask, and 40 ml of a 1 M ammonium acetate aqueous solution (pH 7.0) was added thereto. The mixture was agitated for 60 minutes with a stirrer, and then filtered. The obtained filtrate was measured using an atomic absorption spectrophotometer in the same manner as that in the description above, and the amount of potassium in the target soil was determined.

Based on the amount of potassium release and the amount of potassium in the target soil thus obtained, the potassium release rate was calculated using the following formula.

[Formula 11]

$$\text{Potassium release rate}(\%) = \left(\frac{\text{amount of potassium release on Day 3} - \text{amount of potassium release on Day 0}}{\text{amount of potassium in target soil}}\right) \times 100$$

3c) Activity of Forming Potassium from Compost

Sample soil 100 g was poured into a 250 ml UM sample bottle, and agitated thoroughly. An amount of 3.0 g of the soil was weighed out and poured into a 50 ml conical flask, and distilled water 40 ml was added thereto. The mixture was agitated for 60 minutes with a stirrer and filtered, and the filtrate was used as a potassium extraction liquid. The extraction liquid was supplied to an atomic absorption spectrophotometer in the same manner as above-described 3b), and the amount of potassium was determined and set as the amount of potassium release on Day 0.

Further, bark compost containing culture soil ("Hana-chan Baiyodo" (Hanagokoro, Nagoya)) was added to the sampled soil at an amount of 1% (w/w), followed by thorough agitation. The mixture was left to stand at room temperature for 3 days. An amount of 3.0 g of the soil was weighed out and poured into a 50 ml conical flask, and potassium was extracted using the above-described method. The extract was supplied to the atomic absorption spectrophotometer, and the amount of potassium release was calculated and set as the amount of potassium release on Day 3.

Further, the potassium content in the compost was measured in the same manner as that for the measurement of the potassium content in the target soil described in above 3b) except that compost was used instead of the soil.

Based on the amount of potassium release on Day 0 and Day 3 thus obtained, and the potassium content in the compost, the activity of forming potassium from compost was calculated from the following formula.

[Formula 12]

$$\text{Activity of forming potassium from compost}(\%) = \left(\frac{\text{amount of potassium release on Day 3} - \text{amount of potassium release on Day 0}}{\text{amount of potassium in compost}}\right) \times 100$$

(3-2) Evaluation of Soil Based on Potassium Cycle and Soil Bacteria Count

Figure 5:
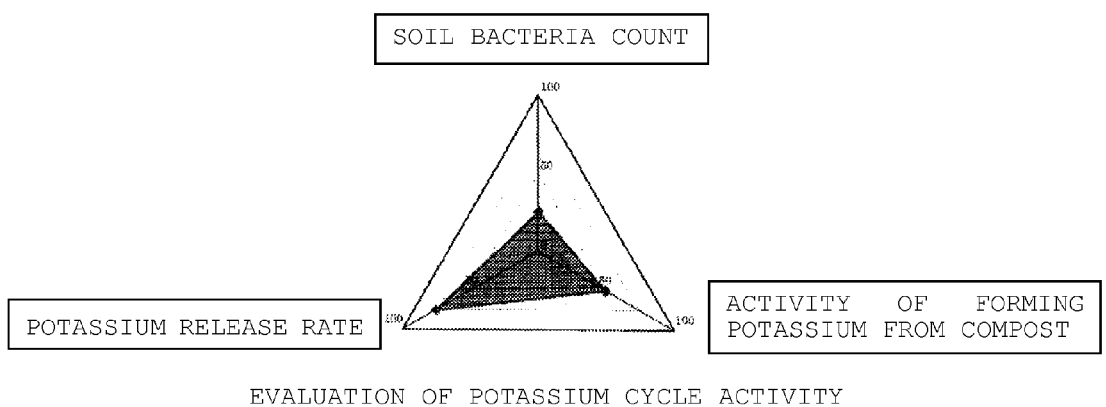
FIG. 5 is a diagram illustrating an example of evaluation of potassium cycle activity for which soil bacteria count, potassium release rate, and activity of forming potassium from compost are used.

With the use of three items, i.e., the soil bacteria count, the potassium release rate, and the activity of forming phosphoric acid from potassium, a chart as shown in FIG. 5 was prepared.

In FIG. 5, the soil bacteria count indicates the proportion of the soil bacteria count in each sample in the case where the average value of the soil bacteria count in agricultural land soil, i.e., 3.25×10$^9$ cells/g-soil is set as 100.

Further, the potassium release rate indicates the potassium release rate in each sample in the case where the activity of completely converting potassium in soil into free potassium in three days is set as 100.

Further, the activity of forming potassium from compost indicates the proportion of the activity of forming potassium from compost in each sample in the case where the activity of completely converting potassium in compost of an amount of 1% (w/w) into free potassium in three days is set as 100.

Still further, in the chart, the area of the triangle whose vertices represent 100 was set as 100, and the relative value of the area of the internal triangle was calculated as a potassium cycle activity indicator for each sample. Table 14 shows the potassium cycle activity indicator for each sample.

TABLE 14

Evaluation value of potassium cycle activity in each sample

| sample No. | evaluation value |
|---|---|
| 11 | 100.00 |
| 12 | 59.5 |
| 13 | 25.3 |
| 14 | 32.8 |
| 15 | 51.4 |
| 16 | 38.1 |
| 17 | 30.8 |
| 18 | 29.6 |
| 19 | 23.5 |
| 20 | 01.8 |

The soil of sample No. 11 has a higher potassium cycle activity indicator, and it can be evaluated that plants are more likely to absorb and use potassium in the soil.

4. Analysis of Relation Between Comprehensive Diagnosis and Vegetation

Relation between comprehensive diagnosis of soil, which is based on the nitrogen cycle activity, the phosphorus cycle activity, and the potassium cycle activity, and vegetation was analyzed using the following methods. As the soil, 10 soil samples (No. 11 to 20) whose purposes and fertilization statuses differ from one another were used.

(4-1) Experimental Method

4a) Analysis of Soil Bacteria Count

The soil bacteria count was determined using the same eDNA analysis method as if above.

4b) Analysis of Nitrogen Cycle Activity

The nitrogen cycle activity was analyzed in the same manner as item 1.

4c) Analysis of Phosphorus Cycle Activity

The phosphoric acid cycle activity was analyzed in the same manner as item 2.

4d) Analysis of Potassium Cycle Activity

The potassium cycle activity was analyzed in the same manner as item 3.

4e) Analysis of Vegetation

The soil samples were poured into raising seedling pots, and 10 seeds of Komatsuna were sown per planting well. The Komatsuna seeds were grown at 25° C. under 6,000 lux for one week. Akadama-soil was laid in 1/5,000a pots, about 1 kg of soil samples were added to the respective pots, and three seedlings of the same height were implanted into each pot. The seedlings were grown at 25° C. under 6,000 lux for three weeks, and the live weight of an above-ground part of Komatsuna was measured. Each soil sample was tested in three pots, and evaluation was conducted based on the average value.

(4-2) Analysis of Relation Between Comprehensive Diagnosis and Vegetation

Based on the sum of the indicators obtained for each soil sample, comprehensive diagnosis of the soil was performed.

Namely, the sum of the indicators was divided by three, and diagnosis was made such that the greater the obtained value was, the higher the quality of the soil was, whereas the lower the obtained value was, the lower the quality of the soil was.

Further, the relation between the diagnosis results and the live weight of Komatsuna was studied. The results are shown in table 15. According to the results, it was estimated that the higher the comprehensive diagnosis result of the soil was, the better the vegetation in the soil was.

Further, table 16 shows diagnosis values obtained from the area of a triangle which is formed with the ammonia reduction rate, the activity of forming phosphoric acid from phytic acid, and the activity of forming potassium from compost as the vertices. According to the results as well, it was estimated that the higher the comprehensive diagnosis result of the soil was, the better the vegetation in the soil was.

Further, it was estimated that with the comprehensive diagnosis performed using the indicators of nitrogen, phosphorus, and potassium in combination instead of independently, it was possible to evaluate the quality of soil suitable for vegetation accurately.

From the above results, it was estimated that the diagnosis method of the present invention is useful for judgment of whether soil is suitable for vegetation, or useful as indicators for improvement of soil.

TABLE 15

Cycle activities and estimation of comprehensive evaluation

| soil No. | soil type | cycle activity | | | comprehensive diagnosis | vegetation |
| | | nitrogen max. 100 | phosphoric acid max. 100 | potassium max. 100 | average of 3 factors max. 100 | (live weight) g |
| --- | --- | --- | --- | --- | --- | --- |
| 11 | culture soil | 100 | 90.1 | 100 | 96.7 | 23.6 |
| 12 | culture soil | 81.6 | 100 | 59.5 | 80.4 | 20.3 |
| 13 | field soil (loam) | 32.4 | 31.1 | 25.3 | 29.6 | 14.2 |
| 14 | field soil (loam) | 71.7 | 37.3 | 32.8 | 47.3 | 18.3 |
| 15 | field soil (loam) | 45.8 | 40.9 | 51.4 | 46.0 | 17.1 |
| 16 | field soil (loam) | 38.4 | 39.7 | 38.1 | 38.7 | 16.3 |
| 17 | field soil (clay) | 33.2 | 39.1 | 30.8 | 34.3 | 15.8 |
| 18 | field soil (clay) | 21.6 | 63.4 | 29.6 | 38.2 | 16.1 |
| 19 | ground soil (sand) | 4.0 | 48.2 | 23.5 | 25.2 | 12.4 |
| 20 | ground soil (sand) | 20 | 0.8 | 1.8 | 7.5 | 7 |

TABLE 16

Comprehensive evaluation value of soil and estimation of vegetation

| soil No. | soil type | ammonia reduction rate max. 100 | activity of forming phosphoric acid from phytic acid max. 100 | activity of forming potassium from compost max. 100 | general diagnosis value(area ratio of triangle) max. 100 | live weight gain of vegetable (g) |
| --- | --- | --- | --- | --- | --- | --- |
| 11 | culture soil | 100 | 90 | 100 | 93.3 | 23.6 |
| 12 | culture soil | 80.5 | 100 | 78.5 | 74.1 | 20.3 |
| 13 | field soil (loam) | 59.1 | 58 | 50.9 | 31.3 | 14.2 |
| 14 | field soil (loam) | 79.5 | 50 | 50 | 34.8 | 18.3 |
| 15 | field soil (loam) | 65.6 | 70 | 80 | 51.5 | 17.1 |
| 16 | field soil (loam) | 63.2 | 65 | 65.5 | 41.7 | 16.3 |
| 17 | field soil (clay) | 57.4 | 65 | 62.4 | 37.9 | 15.8 |
| 18 | field soil (clay) | 40 | 90 | 60 | 38.0 | 16.1 |
| 19 | ground soil (sand) | 14 | 90 | 55 | 23.3 | 12.4 |
| 20 | ground soil (sand) | 39 | 4.0 | 6.0 | 1.4 | 7.0 |

5. Determination of Amount of Substrate to be Introduced for Measurement of Ammonia Cycle Activity

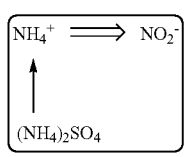

[Chem. 1]

In order to measure the ammonia nitrogen cycle activity in various types of soil, the amount of substrate to be introduced was studied. As the substrate, ammonium sulfate was administered at amounts of 4, 40, and 400 μg-N/g-soil. Then, the amounts of ammonia nitrogen, nitrite nitrogen, and nitrate nitrogen were measured temporally (FIG. 6).

Figure 6:
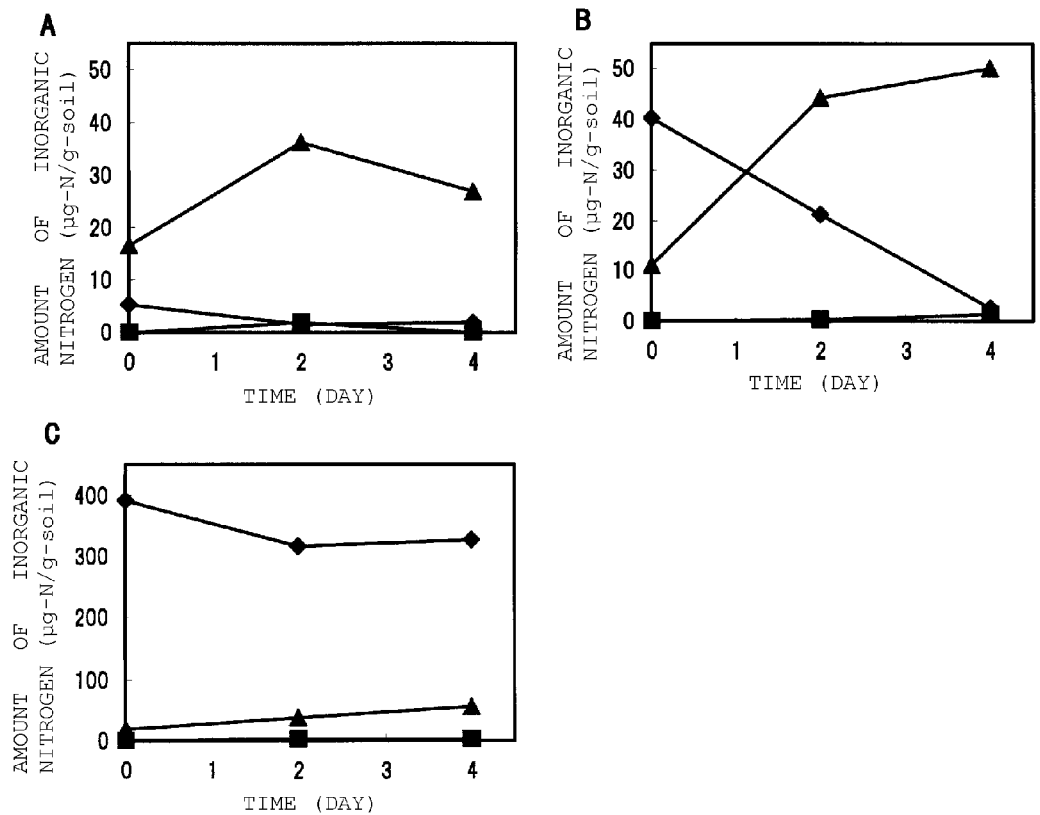
FIG. 6 is a diagram illustrating a nitrogen cycle in soil into which ammonium sulfate was administered. In the diagram, A indicates a case of administration of ammonium sulfate 4 μg-N/g-soil; B indicates a case of administration of ammonium sulfate 40 μg-N/g-soil; and C indicates a case of administration of ammonium sulfate 400 μg-N/g-soil. Symbols indicate as follows. ◆: ammonia nitrogen, ■: nitrite nitrogen, ▲: nitrate nitrogen.

According to FIG. 6, when ammonium sulfate was added at amounts of 4 and 40 μg/g-soil, the ammonia nitrogen was reduced nearly completely on Day 4, whereas nitrate nitrogen was accumulated. When ammonium sulfate was administered at an amount of 400 μg/g-soil, the difference of ammonia nitrogen amount as compared to that at start of the measurement was small.

Ammonia nitrogen contained in various types of agricultural land was measured, and in substantially all the types of soil, the amount of ammonia nitrogen was in the range from 0 to 100 μg-N/g-soil. Thus, based on the following grounds, the amount of ammonia nitrogen to be administered as a substrate was determined.

1) The amount of ammonia nitrogen which enables recognition of significant change in the amount of ammonia nitrogen, and which is generally contained in soil as standard was considered, and it was considered that the amount of the substrate to be introduced might be in a range of 40 to 60 μg/g-soil. In consideration of easiness in calculation, it was finally determined that the amount to be introduced was 60 μg/g-soil.

2) For the sake of quick measurement, it was determined that evaluation is to be conducted on Day 3, when difference in the amount of ammonia nitrogen can be recognized most quickly and assuredly.

6. Determination of Amount of Substrate to be Introduced for Measurement of Nitrite Nitrogen Cycle Activity

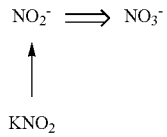

[Chem. 2]

In order to measure nitrite nitrogen cycle activity in various types of soil, the amount of substrate to be introduced was studied. As the substrate, potassium nitrite was administered at amounts of 6, 60, and 600 μg-N/g-soil. Then, the amounts of ammonia nitrogen, nitrite nitrogen, and nitrate nitrogen were measured temporally (FIG. 7).

Figure 7:
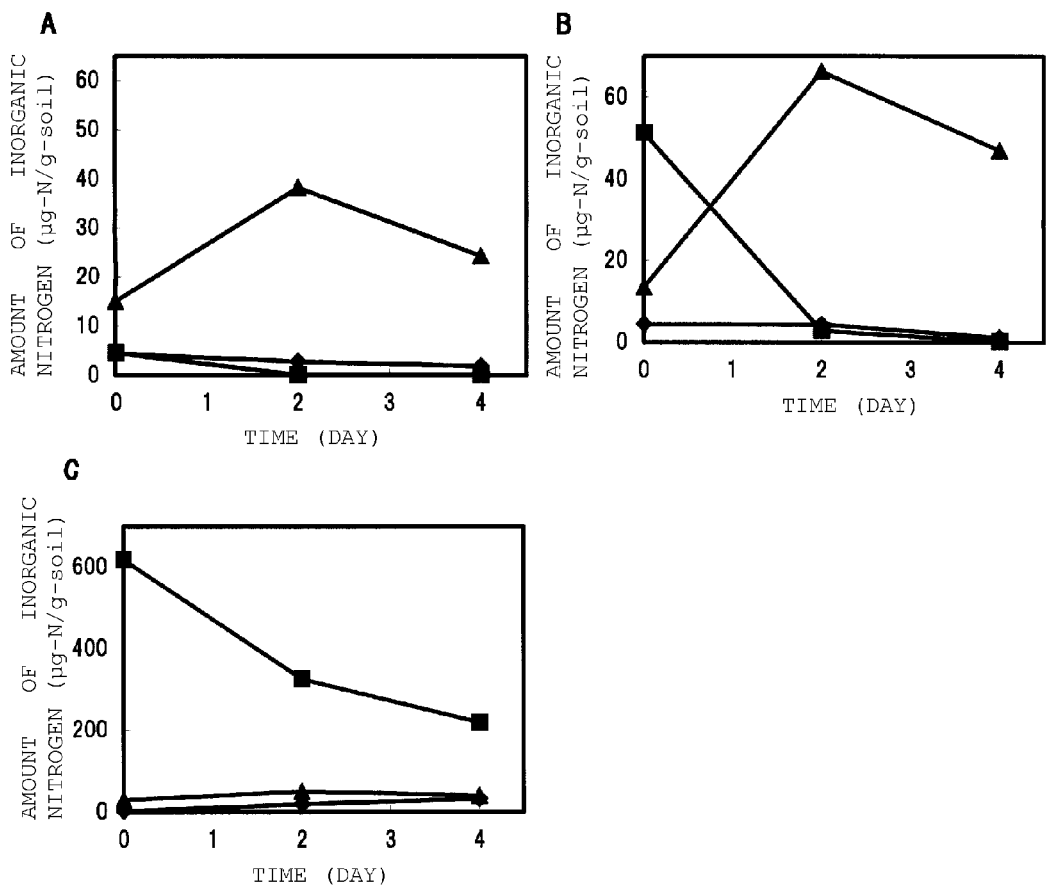
FIG. 7 is a diagram illustrating a nitrogen cycle in soil into which potassium nitrite was administered. In the diagram, A indicates a case of administration of potassium nitrite 6 μg-N/g-soil; B indicates a case of administration of potassium nitrite 60 μg-N/g-soil; and C indicates a case of administration of potassium nitrite 600 μg-N/g-soil. Symbols indicate as follows. ◆: ammonia nitrogen, ■: nitrite nitrogen, ▲: nitrate nitrogen.

According to FIG. 7, when potassium nitrite was added at an amount of 60 μg/g-soil, the nitrite nitrogen was reduced nearly completely on Day 2 to Day 4, whereas nitrate nitrogen was accumulated. When potassium nitrite was administered at an amount of 600 μg/g-soil, temporal reduction of the nitrite nitrogen was recognized. However, when potassium nitrite was administered at an amount of 6 μg/g-soil, the difference of nitrite nitrogen amount as compared to that at start of the measurement was small, and thus the evaluation was difficult.

Nitrite nitrogen was hardly contained in various types of agricultural land soil. However, the nitrate nitrogen was contained at an amount of 0 to 100 μg-N/g-soil which is nearly the same as the amount of ammonia nitrogen. Thus, based on the following grounds, the amount of nitrite nitrogen to be administered as a substrate was determined.

1) The amount of nitrite nitrogen which enables recognition of significant change in the amount of nitrite nitrogen, and which is generally contained in soil as standard was considered. In consideration of easiness in calculation, it was determined that the amount of the substrate to be introduced was 60 μg/g-soil.

2) Similarly to the amount of ammonia nitrogen, it was determined that the evaluation on the change in the amount of nitrite nitrogen is to be conducted on Day 3.

7. Ground for Lower Limit of Bacteria Count

Figure 8:
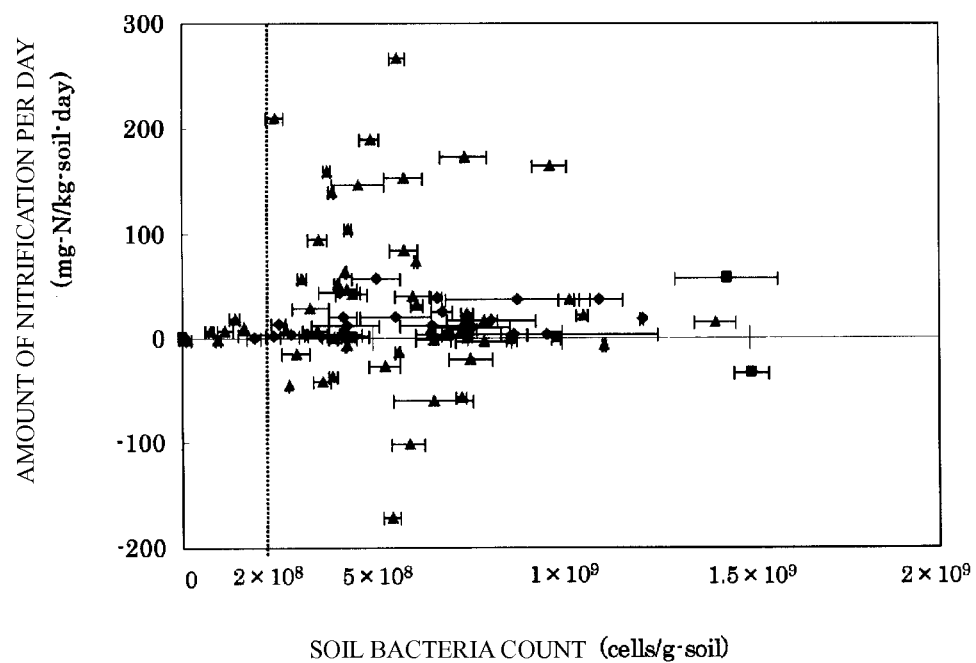
FIG. 8 is a diagram illustrating the relation between the amount of nitrification per day and soil bacteria count. Symbols indicates as follows. ▲: field, ◆: paddy field, ■: land other than agricultural land. Error bars indicate standard deviations.

The relation between the nitrification activity and the bacteria count in various types of soil was studied. FIG. 8 illustrates the amount of nitrification per day. The soil bacteria count was determined using the same eDNA analysis method as if above. The amount of nitrification indicates the sum of the amount of nitrite nitrogen and the amount of nitrate nitrogen measured after ammonia nitrogen was administered into the soil at an amount of 60 λg-N/g dry soil followed by standing for one day. According to the result, it was clarified that when the microorganism count was 200 million/g or less, nitrification reaction stagnates.

8. Lower Limit of Comprehensive Diagnosis Value

If the values of the ammonia reduction rate, the activity of forming phosphoric acid from phytin, and the activity of forming potassium from compost are equal to or less than 30, 10, and 5, respectively, it is not judged that the soil has excellent quality. The proportion of the area of a triangle formed with these lower limits as the vertices with respect to the area of the equilateral triangle formed with the corresponding reference values as the vertices is 1.7 points, the lower limits being located on line segments extending from the center of gravity of the equilateral triangle to the corresponding vertices. Thus, it was judged that if the proportion was lower than the value, favorable vegetation was not expected in the soil.

TABLE 17

| Lower limits of nitrogen, phosphoric acid, potassium, and general diagnosis value | | | |
|---|---|---|---|
| activity of oxidation of ammonia max. 100 | activity of forming phosphoric acid from phytic acid max. 100 | activity of forming potassium from compost max. 100 | general diagnosis value(area ratio of triangle) max. 100 |
| 30 | 10 | 5 | 1.7 |

9. Comparison with Conventional Techniques

In the conventional techniques, the amount of nutrient contained in soil, pH and CEC (base substitution capacity) of soil, and the like were measured, and utilized for production of agricultural crops. However, effects of fertilizer such as compost containing a plenty of organic substances, when added, cannot accurately be recognized from these values.

With the use of sterilized field soil and unsterilized field soil (both of which were derived from the same land), the nitrogen cycle activity and the live weight of Komatsuna were measured (table 18). Compost was added to the sterilized soil and the unsterilized soil at an amount of 2.5%, and the growth of Komatsuna was analyzed. Experimental field soil was used for both.

Chemical properties (chemical analysis values) of both types of soil were the same. However, since the sterilized soil did not contain microorganisms, the nitrogen cycle activity in the sterilized soil was lower (soil was aseptic immediately after sterilization, but since the experiment was performed in an open field, microorganisms entered the soil from the outside, and the microorganism count restored gradually). Thus, the live weight of Komatsuna was lower. Accordingly, the present invention is able to clearly distinguish any types of soil that conventional chemical analyses have not been able to distinguish, and thus contributes to more accurate soil evaluation.

TABLE 18

Table 3 Vegetation in soil having different cycle activities

| soil | treatment | nitrogen cycle activity | live weight of Komatsuna (g) |
|---|---|---|---|
| experimental field soil | sterilized | 10.5 | 2.56 ± 0.2 |
| experimental field soil | unsterilized | 51.9 | 5.05 ± 0.9 |

Six samples were used for each experiment. Chemical analysis values of both types of soil were the same.

The invention claimed is:

1. A soil improvement method comprising:
obtaining soil;
measuring the following (I) to (IV):
(I) an ammonia reduction rate in the soil based on an indophenol method, a leaching method using potassium chloride, or high-performance liquid chromatography;
(II) an activity of forming phosphoric acid from phytic acid in the soil based on a molybdenum blue method or high-performance liquid chromatography; and
(III) an activity of forming potassium from compost in the soil based on atomic absorption spectrophotometry or ICP-MS, and
(IV) a soil bacteria count in soil based on a measurement value found by a method of eluting DNA present in a sample taken from the target soil for diagnosis and determining the amount of the DNA; and
diagnosing a problem with a cycle activity indicator which is calculated using (I) to (III), and a problem with (IV) the soil bacteria count in soil; and
performing treatment for improving the cycle activity indicator in accordance with a result of the diagnosis, wherein the treatment on the soil is selected from the group consisting of administration of fertilizer containing one or more of nitrogen, phosphorus, and potassium, administration of nutrient components for activating soil microorganism, and administration of microorganisms having cycle activities of one or more of nitrogen, phosphorus, and potassium.

2. The method of claim 1, wherein the cycle activity indicator indicates a proportion,
with respect to the area of an equilateral triangle having, as vertices, a preset reference value of an ammonia reduction rate, a preset reference value of an activity of forming phosphoric acid from phytic acid, and a preset reference value of an activity of forming potassium from compost,
of the area of a triangle having, as vertices, points of measured values of (I) the ammonia reduction rate, (II) the activity of forming phosphoric acid from phytic acid, and (III) the activity of forming potassium from compost, the points being located on line segments extending from the center of gravity of the equilateral triangle to the corresponding vertices of the equilateral triangle.

3. A soil improvement method comprising:
obtaining soil;
measuring the following (A-1) to (A-3):
(A-1) a soil bacteria count in the soil based on a measurement value found by a method of eluting DNA present in a sample taken from a target soil for diagnosis and determining the amount of the DNA;
(A-2) an ammonia reduction rate in the soil based on a indophenol method, a leaching method using potassium chloride or high-performance liquid chromatography; and
(A-3) a nitrous acid reduction rate in the soil based on a naphthyl ethylenediamine method or high-performance liquid chromatography, the following (B-1) to (B-3):
(B-1) the soil bacteria count in the soil based on a measurement value found by a method of eluting DNA present in a sample taken from the target soil for diagnosis and determining the amount of the DNA;
(B-2) an activity of forming phosphoric acid from phytic acid in the soil based on a molybdenum blue method or high-performance liquid chromaotography; and
(B-3) an activity of forming phosphoric acid from compost in the soil based on a molybdenum blue method or high-performance liquid chromatography, and the following (C-1) to (C-3):
(C-1) the soil bacteria count in the soil based on a measurement value found by a method of eluting DNA present in a sample taken from the target foil for diagnosis and determining the amount of the DNA;
(C-2) a potassium release rate in the soil based on atomic absorption spectrophotometery or ICP-MS; and
(C-3) an activity of forming potassium from compost in the soil based on atomic absorption spectrophotometry or ICP-MS; and
diagnosing a problem with A) a nitrogen cycle activity indicator which is calculated using (A-1) to (A-3), a problem with B) a phosphorus cycle activity indicator which is calculated using (B-1) to (B-3), and a problem with C) a potassium cycle activity indicator which is calculated using (C-1) to (C-3); and
performing treatment on the soil for improving A) the nitrogen cycle activity indicator, B) the phosphorus cycle activity indicator, and C) the potassium cycle activity indicator in accordance with a result of the diagnosis,
wherein the treatment on the soil is selected from the group consisting of administration of fertilizer containing one or more of nitrogen, phosphorus, and potassium, administration of nutrient components from activating soil microorganism, and administration of microorganisms having cycle activities of one or more of nitrogen, phosphorus, and potassium.

4. The method of claim 3, wherein the nitrogen cycle activity indicator indicates a proportion,
   with respect to the area of an equilateral triangle having, as vertices, a preset reference value of a soil bacteria count, a preset reference value of an ammonia reduction rate, and a preset reference value of a nitrous acid reduction rate,
   of the area of a triangle having, as vertices, points of measured values of (A-1) the soil bacteria count, (A-2) the ammonia reduction rate, and (A-3) the nitrous acid reduction rate, the points being located on line segments extending from the center of gravity of the equilateral triangle to the corresponding vertices of the equilateral triangle.

5. The method of claim 4, wherein the phosphorus cycle activity indicator indicates a proportion,
   with respect to the area of an equilateral triangle having, as vertices, the preset reference value of the soil bacteria count, a preset reference value of an activity of forming phosphoric acid from phytic acid, and a preset reference value of an activity of forming phosphoric acid from compost,
   of the area of a triangle having, as vertices, points of measured values of (B-1) the soil bacteria count, (B-2) the activity of forming phosphoric acid from phytic acid, and (B-3) the activity of forming phosphoric acid from compost, the points being located on line segments extending from the center of gravity of the equilateral triangle to the corresponding vertices of the equilateral triangle.

6. The method of claim 4, wherein the potassium cycle activity indicator indicates a proportion,
   with respect to the area of an equilateral triangle having, as vertices, the preset reference value of the soil bacteria count, a preset reference value of a potassium release rate, and a preset reference value of an activity of forming potassium from compost,
   of the area of a triangle having, as vertices, points of measured values of (C-1) the soil bacteria count, (C-2) the potassium release rate, and (C-3) the activity of forming potassium from compost, the points being located on line segments extending from the center of the gravity of the equilateral triangle to the corresponding vertices of the equilateral triangle.

7. The method of claim 3, wherein the phosphorus cycle activity indicator indicates a proportion,
   with respect to the area of an equilateral triangle having, as vertices, the preset reference value of the soil bacteria count, a preset reference value of an activity of forming phosphoric acid from phytic acid, and a preset reference value of an activity of forming phosphoric acid from compost,
   of the area of a triangle having, as vertices, points of measured values of (B-1) the soil bacteria count, (B-2) the activity of forming phosphoric acid from phytic acid, and (B-3) the activity of forming phosphoric acid from compost, the points being located on line segments extending from the center of gravity of the equilateral triangle to the corresponding vertices of the equilateral triangle.

8. The method of claim 3, wherein the potassium cycle activity indicator indicates a proportion,
   with respect to the area of an equilateral triangle having, as vertices, the preset reference value of the soil bacteria count, a preset reference value of a potassium release rate, and a preset reference value of an activity of forming potassium from compost,
   of the area of a triangle having, as vertices, points of measured values of (C-1) the soil bacteria count, (C-2) the potassium release rate, and (C-3) the activity of forming potassium from compost, the points being located on line segments extending from the center of the gravity of the equilateral triangle to the corresponding vertices of the equilateral triangle.

* * * * *